US006867019B2

(12) United States Patent
Shao et al.

(10) Patent No.: US 6,867,019 B2
(45) Date of Patent: Mar. 15, 2005

(54) ISOLATED HUMAN RAS-LIKE PROTEINS, NUCLEIC ACID MOLECULES ENCODING THESE HUMAN RAS-LIKE PROTEINS, AND USES THEREOF

(75) Inventors: Wei Shao, Frederick, MD (US); Gennady V. Merkulov, Baltimore, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 225 days.

(21) Appl. No.: 09/817,199

(22) Filed: Mar. 27, 2001

(65) Prior Publication Data

US 2002/0142380 A1 Oct. 3, 2002

(51) Int. Cl.[7] .................................................. C12P 21/06

(52) U.S. Cl. .................... 435/69.1; 536/23.4; 536/23.5; 530/350; 435/320.1; 435/325

(58) Field of Search .............................. 536/23.5, 23.1, 536/24.1; 435/320.1, 325, 69.1

(56) References Cited

U.S. PATENT DOCUMENTS 6,426,186 B1 * 7/2002 Jones et al. .................... 435/6
6,569,662 B1 * 5/2003 Tang et al. ................. 435/212

FOREIGN PATENT DOCUMENTS

WO WO-0153312 A1 * 7/2001

OTHER PUBLICATIONS

Boehringer Mannheim Biochemical 1994 Catalog, p. 93.*

DATABASE GenEMBL EST, Accession No. BM921365, NIH–MGC, Mar. 12, 2002 (see USPTO search report US–09–817–199a–2.rst, result 1).*

DATABASE SwissProt 40, Accession No. Q96AX2, Strausberg R, Jun. 15, 2002 (see USPTO search report US–09–817–199a–2.rsp, result 1).*

DATABASE GenEMBL, Accession No. AK098068, Isogai T. et al., Jul. 15, 2002 (see USPTO search report US–09–817–199a–2.rge, result 2).*

* cited by examiner

*Primary Examiner*—Larry R. Helms
*Assistant Examiner*—Stephen L. Rawlings
(74) *Attorney, Agent, or Firm*—Celera Genomics; Justin D. Karjala

(57) ABSTRACT

The present invention provides amino acid sequences of polypeptides that are encoded by genes within the human genome, the Ras-like protein polypeptides of the present invention. The present invention specifically provides isolated polypeptide and nucleic acid molecules, methods of identifying orthologs and paralogs of the Ras-like protein polypeptides, and methods of identifying modulators of the Ras-like protein polypeptides.

11 Claims, 12 Drawing Sheets

```
   1 TTCGCCTGCG GGCCGGCACT GCTCACCTCT CGTCCAGGGA CATGACGGGC
  51 ACGCCAGGCG CCGTTGCCAC CCGGGATGGC GAGGCCCCCG AGCGCTCCCC
 101 GCCCTGCAGT CCGAGCTACG ACCTCACGGG CAAGGTGATG CTTCTGGGAG
 151 ACACAGGCGT CGGCAAAACA TGTTTCCTGA TCCAATTCAA AGACGGGGCC
 201 TTCCTGTCCG GAACCTTCAT AGCCACCGTC GGCATAGACT TCAGGAACAA
 251 GGTGGTGACT GTGGATGGCG TGAGAGTGAA GCTGCAGATC TGGGACACCG
 301 CTGGGCAGGA ACGGTTCCGA AGCGTCACCC ATGCTTATTA CAGAGATGCT
 351 CAGGCCTTGC TTCTGCTGTA TGACATCACC AACAAATCTT CTTTCGACAA
 401 CATCAGGGCC TGGCTCACTG AGATTCATGA GTATGCCCAG AGGGACGTGG
 451 TGATCATGCT GCTAGGCAAC AAGGCGGATA TGAGCAGCGA AAGAGTGATC
 501 CGTTCCGAAG ACGGAGAGAC CTTGGCCAGG GAGTACGGTG TTCCCTTCCT
 551 GGAGACCAGC GCCAAGACTG GCATGAATGT GGAGTTAGCC TTTCTGGCCA
 601 TCGCCAAGGA ACTGAAATAC CGGGCCGGGC ATCAGGCGGA TGAGCCCAGC
 651 TTCCAGATCC GAGACTATGT AGAGTCCCAG AAGAAGCGCT CCAGCTGCTG
 701 CTCCTTCATG TGAATCCCAG GGGGCAGAGA GGAGGCTCTG GAGGCACACA
 751 GGATGCAGCC TTCCCCCTCC CAGGCCTGGC TTATTCCAAG AGGCTGAGCC
 801 AATGGGGAGA AAGATGGAGG ACTCACTGCA CAGCCGCTTC CTAGCAGGGA
 851 GCTATACTCC AACTCCTACT TGAGTTCCTG CGGTCTCCCC GCATCCACAG
 901 GGAGGGTAAA ACACTTAGCT TTTATTTTAA TAGTACATAA TTTAATACCA
 951 AAAAAGGCGC CTGGATCCCC AAAAAACCGA GGCTGGGAGC TAGTGGCCCT
1001 TTTGCTTTCT ACGAGTTGGG GGGGGGGGGC TCGCTCGTAA GGATAAGAAA
1051 GGTGGTGTTG CTCCAGCTCA GCCCCAGGGG ACACAGATGC ACTTTGGGGG
1101 TGAGGGCAGG TAATGACTCC ATCGCACCCT CAGTTCAGCT GGACAGAGGC
1151 TCAGGTGACC CCAGCCTTCA CTGTCTCCCG CTCTCCAGGA GCTTATCTTC
1201 GCCCCATCTC CCAAATAAGT GGGCCCTTGT GCTGTGAGGA AGACCAAAGC
1251 CTCAGGGAAG ATAAGAGATA TGGAGATGGG AGGGGGAGGA CAAGGGGCAG
1301 AGAGTAGGGT CTAGCTGGCT ATCTCTGGCC TTACTAACAC CCCCCTGGAG
1351 GCATGCCCCT TTTCTCCAGC ACACAAGCAC ATTGGGGCAC CTGGAAATAT
1401 TGGTTCCAGG CTCCTGTTCT CTGGACTTCA GATCCTGGGG GAGCCCCTCC
1451 CCCCCCTGAA TCCCTGGCTT AGCTACCTTC CTGCCTGTGC ACCTAAAAAC
1501 CTCAGGTCAG AACTAGGAAA AGAGTTTTGT TTTTATTTTT TTGAAATGGA
1551 GTCTCGTTCT GTCGCCCAGG CTGAGGTGCA GTAGTGCAAT CTCCGCTCAC
1601 TACAACCTCC ACTCCCTGGG GCTCAAGCGA TCCTCCCACC TCAGCCGCCG
1651 AAGTAGCTGG GACTATAGGT GTGTACCATC ACACCTGGCT AATTTTTGTA
1701 TTTTTGTAG ACACAGGGTT TCGCCATGTT GCCCAGGCTG GTCTTGAATT
1751 CCTGAGCTCA AGCAACCTGC CGGCCTCGGC CTCCCAAAGT ACTGGGATTA
1801 CACGCAGAAG GCACCATGCC CAGGCTAGAT GTGTCTTATC CCAATCCTTT
1851 GGCAGGCATG CAGCTCCACA GGCGATTTCT TCAAGCAGCT GAAGTGTTTA
1901 GCCCTCCTGG GTTAAGAGCC AGATAAGGAG AAATCCCTTT CCTAGGTTTG
1951 GAATGTGTTG TGAAAAAAAA GAGAAATCCC TGGCTCCTGG AGCTGGTGGG
2001 AGACAAGATT AAGCAAACCT CCCCTGACAT GTATCCCTTT GACCCCAAGC
2051 TCTGCCTCCT CCCTGACCAC CCATGCCCTT TCCTTTAACT TCTCAAACAG
2101 ATACCAGGGC CTAAACTGCT TTACCTCCCC TCCTACTGAG TCAGGTTAGG
2151 TGGTGGGAGG TCACCCATTT CCGAGTTAAA CCAATGCAAT ATGAGTAAAA
2201 CAAAGTCATG TGGGTATGTC TGGGGTAGAG AGAGGGGTAG CAAGTTCATG
2251 TGTCCTCCTT GGTCACATAT CTCCCAAAGC TCTGATCCCT GCCATGGGAA
2301 GTGGACAGGA AACATGAGGT CATGACCTGC AGGCATCTTT ACTGCAGCTC
2351 TGCCGGCCTG GAGGGGGAGA GGGGGAGGAA GAAGTATGCG CTGCACATTT
2401 CTGAGGCTAC TGCATTTGCT TTCAAGGCAG AAATCTTGCT CTGAGCAGTC
2451 AGCGGCTCCA GTTTGGGCCC GATAAGGAAG TTCTCCGTGG CCTCCCTCAG
2501 GCAGAGCAGG GAGGAGGCTG ACATTGCCAG TCTCTTCTGG GGCCCAAGGC
2551 AGGTTGCAGG AGATCCAATC CCATAGACAG CTCTGGGCCT CTTGCATTTG
2601 AGTTTTTCAG AATTAAACTG CAGTATTTTG GAAAGCAAAA AAAAAAAAAA
2651 AAAAAAAAAA AAAAAAAAAA AAAA   (SEQ ID NO:1)
```

FEATURES:

5'UTR: 1-41
Start Codon: 42
Stop Codon: 711
3'UTR: 714

FIGURE 1A

Homologous proteins:

Top 10 BLAST Hits

| | Score | E |
|---|---|---|
| CRA\|103000001517087 /altid=gi\|10946770 /def=ref\|NP_067386.1\| RA... | 425 | e-117 |
| CRA\|1000682330460 /altid=gi\|7657492 /def=ref\|NP_055168.1\| RAB26... | 297 | 4e-79 |
| CRA\|18000004977238 /altid=gi\|1710022 /def=sp\|P51156\|RB26_RAT RA... | 294 | 3e-78 |
| CRA\|18000005013109 /altid=gi\|1083775 /def=pir\|\|JC2528 GTP-bindi... | 293 | 7e-78 |
| CRA\|89000000198627 /altid=gi\|7296421 /def=gb\|AAF51708.1\| (AE003... | 273 | 9e-72 |
| CRA\|18000005076419 /altid=gi\|7438397 /def=pir\|\|T15123 hypotheti... | 207 | 4e-52 |
| CRA\|18000004912300 /altid=gi\|134236 /def=sp\|P20791\|SAS2_DICDI G... | 203 | 7e-51 |
| CRA\|98000043536338 /altid=gi\|12963499 /def=ref\|NP_075615.1\| cel... | 203 | 9e-51 |
| CRA\|18000004929618 /altid=gi\|131798 /def=sp\|P24407\|RAB8_HUMAN R... | 202 | 1e-50 |
| CRA\|18000004952869 /altid=gi\|131848 /def=sp\|P22128\|RAB8_DISOM R... | 202 | 2e-50 |
| CRA\|18000005221564 /altid=gi\|4586580 /def=dbj\|BAA76422.1\| (AB02... | 202 | 2e-50 |

BLAST dbEST hits:

| | Score | E |
|---|---|---|
| gi\|13033710 /dataset=dbest /taxon=960... | 1318 | 0.0 |
| gi\|12785775 /dataset=dbest /taxon=960... | 1316 | 0.0 |
| gi\|12904236 /dataset=dbest /taxon=960... | 1035 | 0.0 |
| gi\|9093496 /dataset=dbest /taxon=9606... | 694 | 0.0 |

EXPRESSION INFORMATION FOR MODULATORY USE:

library source:

From BLAST dbEST hits:

gi|13033710 prostate
gi|12785775 brain
gi|12904236 T cells from T cell leukemia
gi|9093496 leukopheresis From tissue screening panels:

leukocyte

FIGURE 1B

Docket No.: CL001187
Serial No.: 09/817,199
Inventors: SHAO, Wei et al.
Titl : ISOLATED HUMAN RAS-LIKE PROTEINS...

```
  1 MTGTPGAVAT RDGEAPERSP PCSPSYDLTG KVMLLGDTGV GKTCFLIQFK
 51 DGAFLSGTFI ATVGIDFRNK VVTVDGVRVK LQIWDTAGQE RFRSVTHAYY
101 RDAQALLLLY DITNKSSFDN IRAWLTEIHE YAQRDVVIML LGNKADMSSE
151 RVIRSEDGET LAREYGVPFL ETSAKTGMNV ELAFLAIAKE LKYRAGHQAD
201 EPSFQIRDYV ESQKKRSSCC SFM   (SEQ ID NO:2)
```

FEATURES:

Functional domains and key regions:

[1] PDOC00001 PS00001 ASN_GLYCOSYLATION
N-glycosylation site 114-117 NKSS (SEQ ID NO:5)

[2] PDOC00004 PS00004 CAMP_PHOSPHO_SITE
cAMP- and cGMP-dependent protein kinase phosphorylation site Number of matches: 2

| | | | |
|---|---|---|---|
| 1 | 214-217 | KKRS | (SEQ ID NO:6) |
| 2 | 215-218 | KRSS | (SEQ ID NO:7) |

[3] PDOC00005 PS00005 PKC_PHOSPHO_SITE
Protein kinase C phosphorylation site

Number of matches: 5

| | | |
|---|---|---|
| 1 | 29-31 | TGK |
| 2 | 113-115 | TNK |
| 3 | 149-151 | SER |
| 4 | 173-175 | SAK |
| 5 | 212-214 | SQK |

[4] PDOC00006 PS00006 CK2_PHOSPHO_SITE
Casein kinase II phosphorylation site 116-119 SSFD (SEQ ID NO:8)

[5] PDOC00008 PS00008 MYRISTYL
N-myristoylation site

Number of matches: 5

| | | | |
|---|---|---|---|
| 1 | 3-8 | GTPGAV | (SEQ ID NO:9) |
| 2 | 6-11 | GAVATR | (SEQ ID NO:10) |
| 3 | 39-44 | GVGKTC | (SEQ ID NO:11) |
| 4 | 52-57 | GAFLSG | (SEQ ID NO:12) |
| 5 | 57-62 | GTFIAT | (SEQ ID NO:13) |

[6] PDOC00017 PS00017 ATP_GTP_A
ATP/GTP-binding site motif A (P-loop)

36-43 GDTGVGKT (SEQ ID NO:14)

[7] PDOC00579 PS00675 SIGMA54_INTERACT_1
Sigma-54 interaction domain ATP-binding region A signature 32-45 VMLLGDTGVGKTCF (SEQ ID NO:15)

Membrane spanning structure and domains:

| Helix | Begin | End | Score | Certainty |
|---|---|---|---|---|
| 1 | 48 | 68 | 0.715 | Putative |

FIGURE 2A

```
BLAST Alignment to Top Hit:
>CRA|103000001517087 /altid=gi|10946770 /def=ref|NP_067386.1| RAB37,
          member of RAS oncogene family; GTPase Rab37 [Mus
          musculus] /org=Mus musculus /taxon=10090 /dataset=nraa
          /length=223
         Length = 223

 Score =  425 bits (1081), Expect = e-117
 Identities = 209/223 (93%), Positives = 215/223 (95%)
 Frame = +3

Query: 42  MTGTPGAVATRDGEAPERSPPCSPSYDLTGKVMLLGDTGVGKTCFLIQFKDGAFLSGTFI 221
            MTGTPGA    DGEAPERSPP SP+YDLTGKVMLLGD+GVGKTCFLIQFKDGAFLSGTFI
Sbjct: 1   MTGTPGAATAGDGEAPERSPPFSPNYDLTGKVMLLGDSGVGKTCFLIQFKDGAFLSGTFI 60

Query: 222 ATVGIDFRNKVVTVDGVRVKLQIWDTAGQERFRSVTHAYYRDAQALLLLYDITNKSSFDN 401
            ATVGIDFRNKVVTVDG RVKLQIWDTAGQERFRSVTHAYYRDAQALLLLYDITN+SSFDN
Sbjct: 61  ATVGIDFRNKVVTVDGARVKLQIWDTAGQERFRSVTHAYYRDAQALLLLYDITNQSSFDN 120

Query: 402 IRAWLTEIHEYAQRDVVIMLLGNKADMSSERVIRSEDGETLAREYGVPFLETSAKTGMNV 581
            IRAWLTEIHEYAQRDVVIMLLGNKAD+SSERVIRSEDGETLAREYGVPF+ETSAKTGMNV
Sbjct: 121 IRAWLTEIHEYAQRDVVIMLLGNKADVSSERVIRSEDGETLAREYGVPFMETSAKTGMNV 180

Query: 582 ELAFLAIAKELKYRAGHQADEPSFQIRDYVESQKKRSSCCSFM 710   (SEQ ID NO:2)
            ELAFLAIAKELKYRAG Q DEPSFQIRDYVESQKKRSSCCSF+
Sbjct: 181 ELAFLAIAKELKYRAGRQPDEPSFQIRDYVESQKKRSSCCSFV 223   (SEQ ID NO:4)
```

Hmmer search results (Pfam):

| Model | Description | Score | E-value | N |
|---|---|---|---|---|
| PF00071 | Ras family | 306.9 | 8.4e-90 | 1 |
| CE00060 | CE00060 rab_ras_like | 213.3 | 3.7e-60 | 1 |
| PF01142 | Uncharacterized protein family UPF0024 | 2.6 | 3.4 | 1 |

Parsed for domains:

| Model | Domain | seq-f | seq-t | | hmm-f | hmm-t | | score | E-value |
|---|---|---|---|---|---|---|---|---|---|
| CE00060 | 1/1 | 31 | 191 | .. | 25 | 193 | . | 213.3 | 3.7e-60 |
| PF01142 | 1/1 | 185 | 201 | .. | 444 | 462 | .] | 2.6 | 3.4 |
| PF00071 | 1/1 | 31 | 223 | .] | 1 | 198 | [] | 306.9 | 8.4e-90 |

FIGURE 2B

```
   1 AGGGGAGAGA AAAGACCGCA TACCAGGCCA GGTGCGGTGG CTCACGCTTG
  51 TAATCCCAGC AATTTGGAAG GCCAAGGCAG GCGTATCGCC TGAGGTCAGC
 101 AGTTCCAAAC CAGCCTGTCC AACATGGTGA AGTTCTCTAC TAAGAATACA
 151 AAAATTACCC AGGCGTGGTG GCGTGCACCT GTAGTCCCAG CTGCTCCAGA
 201 GGCTGAGGCA GGAGAATTGC TTGAACCTGG GAGGCAGAGG CTGCAATGCG
 251 CCAAGATCCC GCCACTGCAC TCCAGCCTGG GCGACAGAGT GAGACTCCGT
 301 CTCCGGGAGC CCACGGCATT GAGCAAACCT CGGCATTATT TGCAGCAAGA
 351 GCCTCTGGCA TCCAAATAGC AACCAACACC ACGCCTCTGT AGTGTGCTGC
 401 GCAGCCTCCA CACTCCAGTC TGAGGCTCCC TGTTTGAGTC CCGCCCTATG
 451 CCCAGCTGAG GTTATAGCAC GCTCACCTCC AGAAGAGGTA ACCCAAGCTC
 501 TTTACTCTAC TGGAGATCAC CTCTGTCCCC ACTCTGGGCG CTTCTCCCAG
 551 CTGACAGAAA ATACCTCCAG CTGATGTCAG AAAATACAGG GCTGGAGGCT
 601 GGCGTACAAA GTCAGTCCCC ACAGGCCTAT GGTGGCCCAT AAGCCACGTC
 651 TACCCCTGCT CCTCACCTCC ACACCTAAGT TAAGAATTGC AGGCCGGGCG
 701 CAGTGGCTCA CGCCTGTAAT CCCAGCACTT TGGGAGGCTG AGGTGGGCGG
 751 ACCGCCTGAG GTCAGGAATT TGAGACCAGC TTGGCCAACA TGGCAAAACC
 801 CCGTCTCTAC TAAAAATACA AAAAGAAAAA ATAGCCGGGC CTGATGTCGC
 851 GCACCTGTAA TCCCAGCTAC TCCGGGAGAC TGAGGCGGGA GTATAGCTTG
 901 AACCCGGGAA GCAAAGGTTG CAGTGAGGCG AGATCGCACC ACTGCACTCC
 951 AGGCTGGGCG ACAGAGTGAG ACTCTGTCTG AAAAAAAAAA AAAGTGCAGG
1001 TACCCCTCTC CAGCTCTCCC CTCCCTACAC ATCCCTCAAA CCGTCCCGCT
1051 GTAATGCACC CGCCCTGTTC CTTGGTAACT TGAAGCTGCT TATAGAATGT
1101 GGAGATGGGG GTAATTGAAA GGTCGGCCCA GGCCACAGAG CCCCTGAGCT
1151 CTGCTACCGG CAACCCCAGC TGCACTCCCC ACTCTCTGTC ACCAGGAGCT
1201 GCCGGGTGCC TGGGATATCC TGGCAGCTCT GCTCAAAATG ATCTACGACT
1251 TCATGAATTT ATTTGGCTCC TCCTCGGGGC CAGGGTGAGT GTCATGGGTT
1301 AATAAGGCCG GCCCCGCCTT CAGGAGCGGT CCACTGGGAG ATGTGTGCTG
1351 CGCAGCCCTC TTGCGAAAGC TCTCCCCTGG TGGGACATTC TGGGCACAAC
1401 CAACAGGCCG GGGGAAATGA GAGGTGATCC ATACTAAAGG GTCAAAGTCC
1451 CCGCACCAGG CAGAGGCCCC AAAACACCGC AGCGTACATG TGCTGCAAGG
1501 CGAGTACGGG TTGGTAAACA AAACTATATT CAGATGAGCT CGGGCCGGGT
1551 GACTTAACAG ATGAGGAAGT GTCTCGGGGC CATCGGCGGA GGCGCAGCCC
1601 AGGGGTCCCC AGCTCCCCGC CTCGCCACCT GGGGACAGCC CACGGCCCGG
1651 GGCTCGGGCG CCGCCTGCTG TCGCGGTGCG CAGCGACTAC GGGAACTCTT
1701 CCGCAGCAGA CGGGGTCCCC GCGGCCCGCT CCCCCAGGGG CAAGCAAGCG
1751 ACCACAGGGG ACCGGTCCCG GGGCTGGATG TGGCTCATGT CCGAAGCGCA
1801 CGGAGCCGAG CCGGTGTTGC TCAGGGAGGC TGCCCGCCCC TTCACGCAGA
1851 CCCTGCGGCT CTGCGTGCCC TCAGGGAACA GCAAGGTCCG AGCCGGTGTC
1901 GTCGAGGGGG CGACGGGACG GAGGGAGGAG CCTGAGGGGT CCCGGTCGAG
1951 GGAGGGGAGG AGTGGGCGGG GCGGGGGTGG GGGCCGTTCC CGCGCTCTCC
2001 TTCGCCTGCG GGCCGGCACT GCTCACCTCT CGTCCAGGGA CATGACGGGC
2051 ACGCCAGGCG CCGTTGCCAC CCGGGATGGC GAGGCCCCCG AGCGCTCCCC
2101 GCCCTGCAGT CCGAGCTACG ACCTCACGGG CAAGGTGGGT GGGCCTCTTC
2151 CGTGAGACCC CCGCCCTCCT CGGCGCTAGC CCCTTCCTGG CTGCGTCTGG
2201 GTTGGACTCA GCCCTTCCCC CAGGCAGCTG CGTCTCCCAG AGGAGGGAGG
2251 GAGAGAGGGT CAGGACACAG CCTCTGGGGC CGTCCCAAGC TCTAGGTGTC
2301 TCTGCTGGCT TGGTGGGGGC GGGTCGCGGA AGATCGCAAA AACTGAGTGA
2351 TCCCCCCGCC GGCCCCAACT CAGTTCTCTT CTGCCACACT CTGGCAAATA
2401 TGAGCCCCCG GGAGCCCATG CTTCTTGGTG AGGGTTAAGC GCGCAACTCT
2451 CGGGGCTCAG GCTGGGAAGG GCTGGGAGAT GGGGACCGAA CGGAGACTCG
2501 GAGAGGACGT CCCCTGCTGG CAGAGGAACT GGCGTTAATG CCATTTTCCG
2551 AGCTAAGCTC TTAGTTGAGA TCTGACATCC AGGTTTAAGG CCTGATGTCC
2601 CCCAGCTGCT CCCCTCCCAT TCCACCCGCT GGAGGCACTG CCTCCCACCT
2651 TCCTCCCTGC AGTCGGAAGC CGCTCCTCCC AGAAGGATGT TGCCAGCCGG
2701 CCTGCAGGTC ACTTGGGAAT TTTTCGAACC TGAGAAAGAT TTCAGTGGTT
2751 GGTCTTTCGC ATCCCGCACT TGAGAGAGCT CCAGGGCTGC TCTCTGGGGC
2801 TTGCTCCCTC TACAGGGGTG TCCTGTATGG AAACAGGTAG GGACAGCAGT
2851 GGACTGGTCT GTCGCCTTCC ATCTGTGTCC TTGGAGTGAG CGGGTACCAG
2901 AAACTGAAAG AACTGCTGAG GGAGCCTAGA GCTTCCACTC TTCCTCTGCA
2951 GGGTTGGGGA TGGAGTGAGG GCTGTCCTGG ATTCCGCTGC ATGGCCTTGA
3001 AGGAGACCTG CCTCTCTCTG GGCCTCGGTT TCCTCCCCGA CACCAGGGCT
3051 CACCCTTGCT GGGAGCCTCA GCCTCCACCC CAGTGTTTCG GGGGAAGCCA
```

FIGURE 3A

```
3101 CCCTGCAAGT CATCCGCCCA GAGCCGTTGA GATAGGCGTC CTGTGTGGGC
3151 TTGTGGCAGG AAATGGGCCC CTGCACCCTC GGAGAGGAGG AGCTGCTGTT
3201 GGCCAGGCCC CAGGCTGAGG GGGACTGCCT GACCTTGTTG CCCTGCAAAC
3251 CAGCTGGGTT GTTTGCCTAG GAGGTGGCCA GGCTAGGCAG CTGTTTGTGT
3301 TTGGTGGAAT CACCGAGCTG GGTGGGTAGC TGGCATCGTT TGCTCAAGGC
3351 AGCTGTGATC TGTAAAGTAC ACAAAGACTG GCCCTCCCTC CCTCCTTCCT
3401 GCTCCAGGGC TGGGACCCAG GAGCCAGGGA GGAGTGCAGG CTCCAGAAAG
3451 CTCCTATCCC CCACCCCTTC ATCTGTTCCC TGGCCAAGCG GCATTGGCCG
3501 GAGAGTTGGT CCCCAGCCTC CCCGGGCCTG CCCCAGGGGA GTGAGTCCAG
3551 GACCCTCTGA GAAAGCCTGG CAGGAGCTCC TTGGACCAGA CTAGGGGTGA
3601 TGTGGCCCAC AGGCAGACAG TTCCCACCCT GGGCCACTCT TCCCTGGGTC
3651 TTAGGTGATT CACCACGATG ATGGGCCCTA GCCATTAACA GACTCTAGAA
3701 ATACCTCAAA GACATTATCC CTCCTCCTTC TACCCACTAT GGAAACCATG
3751 CCACAGAAAG GTTAAGGAAT CTTCCTAAAG TCACACAGTA GGCCATTTAC
3801 AAATCAAGAC CCATCCTTCA TACCCCTTCT GCTCAGCCAC CCCTGCCTCT
3851 CCACCAGAGT TAACTAATGC CAGTACCCCA TGCCCACAAC AGGAATGCCT
3901 TTGGGCTCCA CTGTCAATTT CAGAGCCTCA AAAATAATTC AAACCTAGTC
3951 CCTGCTTAAC CCATTAAGCC ACCTAACCAG CAGCTGGGAA ATTCCAGCAT
4001 TGGATCTAGA CCCCTGTTAT CCAAGATTGG AGAACAGTGG GACAAAGTGC
4051 TCCTCTCCAC CATTCCTGCG TGTCCCTGGG GAAGATGAGC AGAGCAGAGC
4101 CAGACAGTAA AGGAGAGGGC CACGCCCCCT CCACAGGTTA CCTCCTTGGT
4151 ACTCCTGCCC GCACTACCCA CAGCAACCCC GGGATGCCGA TCTGCAGCCA
4201 CATGTCCCAT GTGGGAGGTT TCTGCTGAAA GAACTTCCAA CTACACATCT
4251 CCCCACTTCA GTATAAATTT CAACCTTCCC TAATTCATGC AACCTTTTTT
4301 TTTTTTTTTT TTTTTTGAGA CAGAGTGTCG CTCTGTCACC GAGGCTGGAG
4351 TTCAGTGATG CAATCTCGGC TCACTGCAAC CTCTACCTCC TGGGTTCAAG
4401 CTATTCTCCT GTCTCCGCCT CCCAAGTAAC TGGGACTACA GGCGTGTGCC
4451 ACCACTCCTG GCTAGTTTTT TGTATTTTTA GTAGAGATGG GGTTTCACCT
4501 TGTTGGTCAG GCTGGTCTCA AACTCCCAAC TCAGGTGATC CGTCCACTTG
4551 GGCACCCAAA ATGNNNNNNN NNNNNNNNNN NNNNNNNNNN NNNNNNNNNN
4601 NNNNNNNNNN NNNNNNNNNN NNNNNNNNNN NNNNNNNNNN NNNNNNNNNN
4651 NNNNNNNNNN NNNNNNNNNN NNNNNNNNNN NNNNNNNNNN NNNNNNNNNN
4701 NNNNNNNNNN NNNNNNNNNN TTCAAGTACC AGCCTGGCCA ACATGGTAGA
4751 AACCCCGTCT CTACTAAAAA TAAAAAATTA GCCAGGCGAG GTGGTGCATG
4801 CCTATAATCC CAGCTACTCA GGTAGGCTGA GGCAGGAGAA TCATTTAAAC
4851 CTGGGAGGTG GAGGTTGTGG TGAGCCAAGA TCTCGCCATT GCACTCCAGC
4901 CTGGGCAACA AGAGCAAAAC TCCGTCTCAA AAAAAAAAAG AAAGAAAGAA
4951 AGAAAGAAAC TTCCAAATAA ATGTTGTGAC ACAAAAAAAA AAACCCAAAC
5001 AATATTCATT ATAGAGTATG CAAATGACCA TGCCCCACCC CCAGCAGATT
5051 CTGATAGACT CCCTTGGGTG GGAATCCTTG TCCAATATAT TGACACTTCC
5101 CTTTCCTGTC AGTATAGCCC AGCCCATGCG TGTACTCACG AGCGGACGAT
5151 GGATGACACA AGTACACAGA GGGACGGAAT CCCTGCATGG TGTGGCTATG
5201 GGCAAATGTG GCCACTGTCT AGATTGTGCA AATGTGGTGG TTCTCTGGGG
5251 CCACAGAGCA CACTTGGGGA CCTGTTCATG GTGAGGTCTC AACTCCGGCC
5301 TCTAGGAACT TGAATGAGGA CAGGAGGGTC AGAGGGAGAG CCTAGGAGGC
5351 TGAGCCAAGG AGCGTGGAGA GGAGAGACAG GGTGAAGGTG GCGGCTGGCT
5401 TTCTGGAAGC AGGTGGCCTT TGGTGCGGTC AGCATTCGTG CCAGCCCCCT
5451 CTTCTCTGAT CCTCTCCATG TGTCTCTCTC CTGGAATCCC AGAAGCTGCC
5501 CCTGACTCCC CATTAACTGC CTCTGCCCCT ACCCCCTAGG TGATGCTTCT
5551 GGGAGACACA GGCGTCGGCA AAACATGTTT CCTGATCCAA TTCAAAGACG
5601 GGGCCTTCCT GTCCGGAACC TTCATAGCCA CCGTCGGCAT AGACTTCAGG
5651 GTGAGGTGGC TGCAGGCACT TGCTTCCAGC AGAGAGCCAG GGCTGTGGCT
5701 CAGGCATGGG GGGGTTGCCC CCACCTTGCT CACCCTGGCT CCCAGGGACT
5751 CCCGAGGCTC ATGCCTGGAG GGCACACAAC CCGCTCCCCC AAGACCACAG
5801 AGGTGGCCGG GTCAAAGGAG ACTGGGCAAG GTTGGCTCCT TGCCCAACTA
5851 TAGGATGCAA AAAAATGAGA CTGAGTCTTC GATTCCAGCT CCATTCCTGG
5901 GGGACTTCTC CCAAGCAGAG CAGCCGCAGG CACGGCATAA GCTGAATATC
5951 TTGGCCCACA GAGCCCCTGC TCATTGCTCT CCTACCTGGG CCCCTTTGGA
6001 AAGGCCTCAA AGGTCAATCA GTCTTTCTGG AGTTCCCAGA AAGCACAGCC
6051 CTGCACTGGG TTTAAGAGCT GGGCTTGGGC CAGGCATGGT GGCTCTTGCC
6101 TGTATTCCCA GCACTTTGGG AGGCCGAAGC GGTCAGATCA CAAGGTCAGG
6151 AGTTTGAGAC CAGCCTGGCC AACATGGTGA AACCCCGTCT CTACTAAAAA
```

FIGURE 3B

```
6201 TACAAAAATT AGCCAGGTGT AGTGGCACGC TCCTGCAGTC CCAGCTACTC
6251 GGGAGGCTGA GGCAGGAGAA TCGCTCAAAT CCGGGTGGTG GAGGTTGCAG
6301 TGAGCTGAGA TCGCGCCACT GCACTCCAGC CTGGGCAACA AAGTGAGACT
6351 GCGTCTCAGA AAAAAAAAAA AAAAAAGAGC TGGGCTGGCC ATGTTGGGAG
6401 ACAGCAGCTC ACCAGGGACC CTCCCTCTCA CCTTGACGAC TCCATCTTAC
6451 AAATCTGCAT CAGGGATGCT AGACGCTGCA CACCTGAAGT GTTCAATAGA
6501 GAAAAGGTCT CACCCTGGCA GGTGGGGCTC TACAGCTTCA AGCAGGCAGA
6551 AAGCGAACAC TTCCTTCACT AGAGAATTAG TGGGCAGCTA AAGAAAAGGT
6601 GCTGCTGCAG ATGTAGCCTC AGGTCCCCAG GATGCAGGCA AACACCCCAT
6651 CTCCAGGGGC TCGGTCACAG TCCCAAGGCT AGGCTCCAGG AGAGGGAGAC
6701 CGAAGTGGGG AAAGGGCAGG GCCTCCAGCA GCAACCAGCC CTCCAGCCCT
6751 GGGCTGCCTG ATCCCTGGAG AGAGCCAGGA TGTTTCTCAG GCTCCTCTTG
6801 CCCTGCTGTT GTGAGAAGGC AGTTACAGTC CTCAGAAGGG ACGACTCCAC
6851 AGTGGAGGTG TCTGGGTATG GGGTTCCTGC TGCCCTGATG GTATGATCTG
6901 GCTGGAGACG GTTCTGGGGC TCACTGCACC CACTCTAGGC CTGGAGAGGG
6951 AACAAGAGAG GACGTCTGCA GAGCTGAGGA GCCACATGAC TCCTGCCCTC
7001 CCATCCTCTG CCTTTTTCTC TTTCAGAACA AGGTGGTGAC TGTGGATGGC
7051 GTGAGAGTGA AGCTGCAGGT GAGACCAGAG GCTGGAGTTG GGGAGGGAGG
7101 ATGGAGGACC TGCCCTTCCT TCTCACCCTG AACCACAGGA GGCCTGCAGC
7151 CCTGCCCTCC GCCTGGGGCA ATTTCCTGTG GGGCCCACGG GAGGAAATGG
7201 CTTTTGTTTA TTTGACATCT GCAGAAAAAG CAGTTCCCAG GCACCCTCTC
7251 ATCTATGAAC AGCAGCTCCA AATGCCTTCA GACAAGCTTA GCCTCCATCC
7301 ATCTCCTCCC CAGTTGCCAG GGCTTTATCT GCTCTTAGGA GATTGGACAT
7351 CCCCAACCCC TGAGCTAGGG GAGAGGAGAA GATTCTTTTT TTTTCTTTTC
7401 TTTTCTTTTT TTTTTTGAGA TGGAGTCTCG CTCTGTCGCC CAGGCTGGAG
7451 TGCAGTGGCA CAATCTCGGC TCACTGCAAC CTCTGCCTCC CAGGTTTAAG
7501 AGATTCTCCT GCCTCAGCCT CCTGAGTAGC TGAGACTACA GGTGCATGCC
7551 ACCACACCTG GCTAATTTTT TGTATTTTTA GTAGAGACGG GGTTTCACTG
7601 TGTTAGCCAG GATGGTCTGG ATCTCCTGAC CTCGTGATCC GCCTGCCTCG
7651 GCCTCCCAAA GTGCTGGGAT TACAGGTGTA AGCCACCGCG CTCGGCTGAG
7701 GAGATGATTT TGAACGAGCT TGAGAAATCA GTAACTGCTA CTGTCCAGGT
7751 CATTGGATGC TCAGGGGCTC ATGAGAACCT AAAGAAGAAA ACAGCCCCAC
7801 CTTCCCACAG ATATCTCATA CAACAAAGCA GGCCTGCTCC ACCCAGCACA
7851 TTCCTTGCAC CTGCCTCCTT CTGACCATTT CTCCATCCCA TCCCTTCCCA
7901 GATCTGGGAC ACCGCTGGGC AGGAACGGTT CCGAAGCGTC ACCCATGCTT
7951 ATTACAGAGA TGCTCAGGGT GAGTCCCTCG CACCCTCCAA CCCCTACCCC
8001 AGCCCCTTGG TAGCATCCGT GCTGCTGCCT AAGTCCCCTC TGTGATCCTC
8051 TCCCCTCCAG CCTTGCTTCT GCTGTATGAC ATCACCAACA AATCTTCTTT
8101 CGACAACATC AGGGTAGGTC CTCCCTTCCC CTGACTCCCA CCCATAAGCA
8151 GCCAAGGCAA GGTCTATGCA GGCTGGGGTT GCTTCCTGCC CTGTGGAAAG
8201 CGGGTGGAGC GTGGAGTCCT CCTGCCTTCT GAAAAACACC TACTTGTGAC
8251 TCAGAAGTCA TATCTGCTGC TTTGTATTTG GTGGCCATGT GGGCATGAAG
8301 GCCAAGCAGG CTGTTGTGAC CCTGTGCCAC CTGCATAGCC CTCACTGTGA
8351 TTCACGAGTG TGTTTCGTGA CAAAGTGTTC AGAACAGCCC CCACTCCACC
8401 CTGGATAATT ATCCACAGAG ACCAAGGGAA AAACACAACC AGAAAAGTCC
8451 ACACATACAT CCAGGGCAAG TTGCAAGAAA GTGACTCAGT CAGACAGAGT
8501 GAGTGGTTGT ATCCTCACAA CCAAACTATT ATAGAGACAA AAATTTGATA
8551 AATTCAAGCA CCAATTTTGT TCACGACATT GTATAGGTTT CATGAATCCC
8601 CTGACCTCAA GGACAGTTTG CTGATAAGCA AACTAGGAGA ATAAAACGTT
8651 TATATAGAAA GAGGAAAATC CATGGCACTC ATACTCCTAC CTCCAACCCC
8701 ATGCTCATGG CAGACATCAC TAATCAATCA CAGTACTTTT GATCACTGAA
8751 ACCCTTATGT GGTCTTAGAA TCTTTAACAG GACACTCCAA GAAATCACTG
8801 CTGACAGCCA ACTGATTTGT GAGATAAGGT CTCCATGCAT CTGGATCTTC
8851 CATAGAACTG ATAGTTGCAC AGCATAAAAT GGTGAGGGTG GGGCCATTGT
8901 GGGTTGAGCC ACCAAGGAAG GCCATCCAGG CCTGGATGGG CCAGAACAAA
8951 GGTACAGATG AGAGAACGCA CAGGGTATCG TGTTCAAGGT AGTGAGTAAC
9001 TGAGGATAGT CAAACGGAGC AGAAGAAGAA AGGGGCAGCA GGAGGAAGAG
9051 AATGCCAGTC TCGCACGCCC TCTCCCACAG GCCTGGCTCA CTGAGATTCA
9101 TGAGTATGCC CAGAGGGACG TGGTGATCAT GCTGCTAGGC AACAAGGTGA
9151 GTGGCTCCGG GGCAGGGTCA GCCCAGCCCT GCACTTCCTC AGCCCTAGCC
9201 GGCCCCATAA CCACCCAAGA ACAGTTATCT AGGCATCCTT CCTGAAAAGG
9251 ACTCTGCAGC CTCCAGCTCA GGGGTCAGAC ATATCTGGAG GCTTCTGCCC
```

FIGURE 3C

9301 ATCCCATCTG CCCCTTCCAG GGAAAGTCCA AGTTGTTGCC TGAGAAATCA
9351 AGGGGTGCCC AGTTCTCAGC CCCCATTAGA GCAGAGTGAA CAGGTCCCA
9401 GGTCAGGGGC TAAGAGTGCA AAGGGTTAGC CCCAACTGCT GTCCTATTCC
9451 AAGACCCTTT ACCAAAGGTG AGATCCCAGA GCTGGGAGCT ACACTGGGCA
9501 GAAACCCTGG CCCCAGGCCA ATCACACCTG CCTGCAGTCC CTTGGGCCAC
9551 CAGCAGAGGG CAGGCAACGC CTGCTTCTGG GGCAAAATAT GGGCCCGCTG
9601 GGGCGGAGGC CTCCTTCCCC AGAGTGACCC ATTTGGGCTT GACAGGCGGA
9651 TATGAGCAGC GAAAGAGTGA TCCGTTCCGA AGACGGAGAG ACCTTGGCCA
9701 GGGTAAGTGA TTGTCTGTGG GACAGGGTGA AGGGTGGGGG CAACCCGACG
9751 CTGGCCCTGA GGACACTCTC TCCCGGGCAG GAGTACGGTG TTCCCTTCCT
9801 GGAGACCAGC GCCAAGACTG GCATGAATGT GGAGTTAGCC TTTCTGGCCA
9851 TCGCCAAGTG AGAGCTGGGC AGGGAAGGGA AGTGTGCGGG GCAGGGCGGC
9901 ACACTCCAGG AATCCAGTAG GGCCCGGCCC CTGGCCCAGC CCCTGGACAC
9951 ACCTGCATTC TGCAGGCTGA GGTCCATTTG CTCTGGGAGC ACTGGGCCAC
10001 TGGGAGAGGG GAGGGGGCGG CTCAGCTCCT CACCCCAGCC CAGCCCAGCC
10051 CAGCCCAGCC CATTGTCTCT TCTTCAAGGG AACTGAAATA CCGGGCCGGG
10101 CATCAGGCGG ATGAGCCCAG CTTCCAGATC CGAGACTATG TAGAGTCCCA
10151 GAAGAAGCGC TCCAGCTGCT GCTCCTTCAT GTGAATCCCA GGGGGCAGAG
10201 AGGAGGCTCT GGAGGCACAC AGGATGCAGC CTTCCCCCTC CCAGGCCTGG
10251 CTTATTCCAA GAGGCTGAGC CAATGGGGAG AAAGATGGAG GACTCACTGC
10301 ACAGCCGCTT CCTAGCAGGG AGCTATACTC CAACTCCTAC TTGAGTTCCT
10351 GCGGTCTCCC CGCATCCACA GGGAGGGTAA AACACTTAGC TTTTATTTTA
10401 ATAGTACATA ATTTAATACC AAAAAAGGCG CCTGGATCCC CAAAAAACCG
10451 AGGCTGGGAG CTAGTGGCCC TTTTGCTTTC TAGGACTTGG GGGGCCGGCC
10501 CTCCCTCCTA AGCATAACAA AGGTGGTGTT GCTCCAGCTC AGCCCCAGGG
10551 GACACAGATG CACTTTGGGG GTGAGGGCAG GTAATGACTC CATCGCACCC
10601 TCAGTTCAGC TGGACAGAGG CTCAGGTGAC CCCAGCCTTC ACTGTCTCCC
10651 GCTCTCCAGG AGCTTATCTT CGCCCCATCT CCCAAATAAG TGGGCCCTTG
10701 TGCTGTGAGG AAGACCAAAG CCTCAGGGAA GATAAGAGAT ATGGAGATGG
10751 GAGGGGGAGG ACAAGGGGCA GAGAGTAGGG TCTAGCTGGC TATCTCTGGC
10801 CTTACTAACA CCCCCCTGGA GGCATGCCCC TTTTCTCCAG CACACAAGCA
10851 CATTGGGGCA CCTGGAAATA TTGGTTCCAG GCTCCTGTTC TCTGGACTTC
10901 AGATCCTGGG GGAGCCCCTC CCCCCCCTGA ATCCCTGGCT TAGCTACCTT
10951 CCTGCCTGTG CACCTAAAAA CCTCAGGTCA GAACTAGGAA AAGAGTTTTG
11001 TTTTTATTTT TTTGAAATGG AGTCTCGTTC TGTCGCCCAG GCTGAGGTGC
11051 AGTAGTGCAA TCTCCGCTCA CTACAACCTC CACTCCCTGG GGCTCAAGCG
11101 ATCCTCCCAC CTCAGCCGCC GAAGTAGCTG GGACTATAGG TGTGTACCAT
11151 CACACCTGGC TAATTTTTGT ATTTTTTGTA GACACAGGGT TTCGCCATGT
11201 TGCCCAGGCT GGTCTTGAAT TCCTGAGCTC AAGCAACCTG CCGGCCTCGG
11251 CCTCCCAAAG TACTGGGATT ACACGCAGAA GGCACCATGC CCAGGCTAGA
11301 TGTGTCTTAT CCCAATCCTT TGGCAGGCAT GCAGCTCCAC AGGCGATTTC
11351 TTCAAGCAGC TGAAGTGTTT AGCCCTCCTG GGTTAAGAGC CAGATAAGGA
11401 GAAATCCCTT TCCTAGGTTT GGAATGTGTT GTGAAAAAAA AGAGAAATCC
11451 CTGGCTCCTG GAGCTGGTGG GAGACAAGAT TAAGCAAACC TCCCCTGACA
11501 TGTATCCCTT TGACCCCAAG CTCTGCCTCC TCCCTGACCA CCCATGCCCT
11551 TTCCTTTAAC TTCTCAAACA GATACCAGGG CCTAAACTGC TTTACCTCCC
11601 CTCCTACTGA GTCAGGTTAG GTGGTGGGAG GTCACCCATT TCCGAGTTAA
11651 ACCAATGCAA TATGAGTAAA ACAAAGTCAT GTGGGTATGT CTGGGGTAGA
11701 GAGAGGGGTA GCAAGTTCAT GTGTCCTCCT TGGTCACATA TCTCCCAAAG
11751 CTCTGATCCC TGCCATGGGA AGTGGACAGG AAACATGAGG TCATGACCTG
11801 CAGGCATCTT TACTGCAGCT CTGCCGGCCT GGAGGGGGAG AGGGGGAGGA
11851 AGAAGTATGC GCTGCACATT TCTGAGGCTA CTGCATTTGC TTTCAAGGCA
11901 GAAATCTTGC TCTGAGCAGT CAGCGGCTCC AGTTTGGGCC CGATAAGGAA
11951 GTTCTCCGTG GCCTCCCTCA GGCAGAGCAG GGAGGAGGCT GACATTGCCA
12001 GTCTCTTCTG GGGCCCAAGG CAGGTTGCAG GAGATCCAAT CCCATAGACA
12051 GCTCTGGGCC TCTTGCATTT GAGTTTTTCA GAATTAAACT GCAGTATTTT
12101 GGAAAGCACA TCCTGTCCAC TGTTTCTTTG AAGTGAGTGG GGGGGGGGGG
12151 TCTTGTTGAA GGAATTGTCA TTCACTGCCA AAATCATTCC ATCCTCCTTC
12201 CTCAGTGTCT GTCCTCAGAT GGTCAGCTCC CCGCTCAACA GACTGTCTCC
12251 CGCCTCTGTG ACCAGCCTCT CTTTGGCAAG AGGGAGCTAG AAGGCTTTAC
12301 AGTCCTAATC ATTTTTCTGT TGGAAAAAAA AAAAAAAAAC CAAGGCTCCT
12351 TTCCCTGTGG CGTGTACCCA GAGGTTGATT ACCTGAGTCT GTCCTGCCTC

FIGURE 3D

```
12401 TCCCCACCCC ACCTCCCTAG CCAAACGCTG CTGCCAAAGC CCACGCTATT
12451 GCCCTAGATG GCCTGTCTTC AGCGGGCTGC CCCTCGAGGT CCCAGGCTCT
12501 CCGCGGAGCC CTCACCTTCC CAGCAGGGAT CAGAACCTGC ACTCCTCTAT
12551 GCGAGTCCTG GGACAGCACA AAGTGGATTA GGGTTAGGGT TCCCACAAAC
12601 GGAAAAATGT TATTCAAACA ACTCTGTAGG GTCCGAGGAG GCCCTCCGTC
12651 TTAATTCTCG AGACTGACCG GCCCTCGCTG CCCCGAGCGG GAGCAGTTGC
12701 CCCGGCAACA GCCGCTCCCT CTCAACTGGA GCTGCACCCA GGCTTTGGCT
12751 AAAGGCTGTT AAAACGTTGG CCAGGTGCGG AGGCTCACGT CTGTAATCCC
12801 AGGGCGGATC ACCTGAGGTC AGGAGTTTGA AACCATCCTG GCCAACATGG
12851 CGAAATTTCG TCTCTACTAA AAATACAAAA ATTAGCGGGG CGTGGTGGTG
12901 CGCGCCTGTA ACCCCAGCTG CTCGGGAGGC TGAGGCAGGG GAATCGCTTG
12951 AACCCGGGAG GCGGAGGTTG CAGTGATCCG AGATCGCGCC ACGGCAGTCC
13001 AGCCTGGGCG ACAGAGCGAG ACTCCGTCTC AAAAAAAAAA AAAAAAGTTA
13051 GGGTCCTTTA CCCGAGGGCC GGCTTTCCTC ACTCCCCGCC ACAGGTAGGG
13101 GAAACCAGGC CGGAGCCGGC GGGCCCACCC GCCCAGAACC GGGAATTCGG
13151 CGAGCCCCGC CCCTGCCACC CCAGCGCCGG CC (SEQ ID NO:3)
```

FEATURES:

| | |
|---|---|
| Start: | 2042 |
| Exon: | 2042-2134 |
| Intron: | 2135-5539 |
| Exon: | 5540-5650 |
| Intron: | 5651-7026 |
| Exon: | 7027-7068 |
| Intron: | 7069-7901 |
| Exon: | 7902-7968 |
| Intron: | 7969-8060 |
| Exon: | 8061-8113 |
| Intron: | 8114-9080 |
| Exon: | 9081-9146 |
| Intron: | 9147-9645 |
| Exon: | 9646-9702 |
| Intron: | 9703-9780 |
| Exon: | 9781-9857 |
| Intron: | 9858-10078 |
| Exon: | 10079-10181 |
| Stop: | 10182 |

CHROMOSOME MAP POSITION:

Chromosome # 17

ALLELIC VARIANTS (SNPs):

DNA

| Position | Major | Minor | Domain |
|---|---|---|---|
| 4259 | C | T | Intron |
| 4325 | G | T | Intron |
| 4348 | G | A | Intron |
| 4924 | G | A | Intron |
| 4983 | - | A | Intron |
| 6710 | A | G | Intron |
| 8624 | A | G | Intron |
| 8661 | G | A | Intron |
| 11754 | T | C | Beyond ORF(3') |
| 11836 | A | G | Beyond ORF(3') |

FIGURE 3E

Context:

DNA
Position

4259
ACCCATTAAGCCACCTAACCAGCAGCTGGGAAATTCCAGCATTGGATCTAGACCCCTGTT
ATCCAAGATTGGAGAACAGTGGGACAAAGTGCTCCTCTCCACCATTCCTGCGTGTCCCTG
GGGAAGATGAGCAGAGCAGAGCCAGACAGTAAAGGAGAGGGCCACGCCCCCTCCACAGGT
TACCTCCTTGGTACTCCTGCCCGCACTACCCACAGCAACCCCGGGATGCCGATCTGCAGC
CACATGTCCCATGTGGGAGGTTTCTGCTGAAAGAACTTCCAACTACACATCTCCCCACTT
[C,T]
AGTATAAATTTCAACCTTCCCTAATTCATGCAACCTTTTTTTTTTTTTTTTTTTTTGAG
ACAGAGTGTCGCTCTGTCACCGAGGCTGGAGTTCAGTGATGCAATCTCGGCTCACTGCAA
CCTCTACCTCCTGGGTTCAAGCTATTCTCCTGTCTCCGCCTCCCAAGTAACTGGGACTAC
AGGCGTGTGCCACCACTCCTGGCTAGTTTTTGTATTTTAGTAGAGATGGGGTTTCACC
TTGTTGGTCAGGCTGGTCTCAAACTCCCAACTCAGGTGATCCGTCCACTTGGGCACCCAA (SEQ ID NO:16)

4325
GATTGGAGAACAGTGGGACAAAGTGCTCCTCTCCACCATTCCTGCGTGTCCCTGGGGAAG
ATGAGCAGAGCAGAGCCAGACAGTAAAGGAGAGGGCCACGCCCCCTCCACAGGTTACCTC
CTTGGTACTCCTGCCCGCACTACCCACAGCAACCCCGGGATGCCGATCTGCAGCCACATG
TCCCATGTGGGAGGTTTCTGCTGAAAGAACTTCCAACTACACATCTCCCCACTTCAGTAT
AAATTTCAACCTTCCCTAATTCATGCAACCTTTTTTTTTTTTTTTTTTTTTGAGACAGA
[G,T]
TGTCGCTCTGTCACCGAGGCTGGAGTTCAGTGATGCAATCTCGGCTCACTGCAACCTCTA
CCTCCTGGGTTCAAGCTATTCTCCTGTCTCCGCCTCCCAAGTAACTGGGACTACAGGCGT
GTGCCACCACTCCTGGCTAGTTTTTGTATTTTAGTAGAGATGGGGTTTCACCTTGTTG
GTCAGGCTGGTCTCAAACTCCCAACTCAGGTGATCCGTCCACTTGGGCACCCAAAATG (SEQ ID NO:17)

4348
TGCTCCTCTCCACCATTCCTGCGTGTCCCTGGGGAAGATGAGCAGAGCAGAGCCAGACAG
TAAAGGAGAGGGCCACGCCCCCTCCACAGGTTACCTCCTTGGTACTCCTGCCCGCACTAC
CCACAGCAACCCCGGGATGCCGATCTGCAGCCACATGTCCCATGTGGGAGGTTTCTGCTG
AAAGAACTTCCAACTACACATCTCCCCACTTCAGTATAAATTTCAACCTTCCCTAATTCA
TGCAACCTTTTTTTTTTTTTTTTTTTTTGAGACAGAGTGTCGCTCTGTCACCGAGGCTG
[G,A]
AGTTCAGTGATGCAATCTCGGCTCACTGCAACCTCTACCTCCTGGGTTCAAGCTATTCTC
CTGTCTCCGCCTCCCAAGTAACTGGGACTACAGGCGTGTGCCACCACTCCTGGCTAGTTT
TTGTATTTTAGTAGAGATGGGGTTTCACCTTGTTGGTCAGGCTGGTCTCAAACTCCCA
ACTCAGGTGATCCGTCCACTTGGGCACCCAAAATG (SEQ ID NO:18)

4924
TTCAAGTACCAGCCTGGCCAACATGGTAGAAACCCCGTCTCTACTAAAAATAAAAAATTA
GCCAGGCGAGGTGGTGCATGCCTATAATCCCAGCTACTCAGGTAGGCTGAGGCAGGAGAA
TCATTTAAACCTGGGAGGTGGAGGTTGTGGTGAGCCAAGATCTCGCCATTGCACTCCAGC
CTGGGCAACAAGAGCAAAACTCC
[G,A]
TCTCAAAAAAAAAAAGAAAGAAAGAAAGAAAGAAACTTCCAAATAAATGTTGTGACACAA
AAAAAAAAACCCAAACAATATTCATTATAGAGTATGCAAATGACCATGCCCCACCCCCAG
CAGATTCTGATAGACTCCCTTGGGTGGGAATCCTTGTCCAATATATTGACACTTCCCTTT
CCTGTCAGTATAGCCCAGCCCATGCGTGTACTCACGAGCGGACGATGGATGACACAAGTA
CACAGAGGGACGGAATCCCTGCATGGTGTGGCTATGGGCAAATGTGGCCACTGTCTAGAT (SEQ ID NO:19)

4983
TTCAAGTACCAGCCTGGCCAACATGGTAGAAACCCCGTCTCTACTAAAAATAAAAAATTA
GCCAGGCGAGGTGGTGCATGCCTATAATCCCAGCTACTCAGGTAGGCTGAGGCAGGAGAA
TCATTTAAACCTGGGAGGTGGAGGTTGTGGTGAGCCAAGATCTCGCCATTGCACTCCAGC
CTGGGCAACAAGAGCAAAACTCCGTCTCAAAAAAAAAAAGAAAGAAAGAAAGAAAGAAAC
TTCCAAATAAATGTTGTGACAC

FIGURE 3F

[-,A]
AAAAAAAAAACCCAAACAATATTCATTATAGAGTATGCAAATGACCATGCCCCACCCCCA
GCAGATTCTGATAGACTCCCTTGGGTGGGAATCCTTGTCCAATATATTGACACTTCCCTT
TCCTGTCAGTATAGCCCAGCCCATGCGTGTACTCACGAGCGGACGATGGATGACACAAGT
ACACAGAGGGACGGAATCCCTGCATGGTGTGGCTATGGCAAATGTGGCCACTGTCTAGA
TTGTGCAAATGTGGTGGTTCTCTGGGGCCACAGAGCACACTTGGGGACCTGTTCATGGTG (SEQ ID NO:20)

6710 CACCAGGGACCCTCCCTCTCACCTTGACGACTCCATCTTACAAATCTGCATCAGGGATGC
TAGACGCTGCACACCTGAAGTGTTCAATAGAGAAAAGGTCTCACCCTGGCAGGTGGGGCT
CTACAGCTTCAAGCAGGCAGAAAGCGAACACTTCCTTCACTAGAGAATTAGTGGGCAGCT
AAAGAAAAGGTGCTGCTGCAGATGTAGCCTCAGGTCCCCAGGATGCAGGCAAACACCCCA
TCTCCAGGGGCTCGGTCACAGTCCCAAGGCTAGGCTCCAGGAGAGGGAGACCGAAGTGGG
[A,G]
AAAGGGCAGGGCCTCCAGCAGCAACCAGCCCTCCAGCCCTGGGCTGCCTGATCCCTGGAG
AGAGCCAGGATGTTTCTCAGGCTCCTCTTGCCCTGCTGTTGTGAGAAGGCAGTTACAGTC
CTCAGAAGGGACGACTCCACAGTGGAGGTGTCTGGGTATGGGGTTCCTGCTGCCCTGATG
GTATGATCTGGCTGGAGACGGTTCTGGGGCTCACTGCACCCACTCTAGGCCTGGAGAGGG
AACAAGAGAGGACGTCTGCAGAGCTGAGGAGCCACATGACTCCTGCCCTCCCATCCTCTG (SEQ ID NO:21)

8624 GTGCCACCTGCATAGCCCTCACTGTGATTCACGAGTGTGTTTCGTGACAAAGTGTTCAGA
ACAGCCCCCACTCCACCCTGGATAATTATCCACAGAGACCAAGGGAAAAACACAACCAGA
AAAGTCCACACATACATCCAGGGCAAGTTGCAAGAAAGTGACTCAGTCAGACAGAGTGAG
TGGTTGTATCCTCACAACCAAACTATTATAGAGACAAAAATTTGATAAATTCAAGCACCA
ATTTTGTTCACGACATTGTATAGGTTTCATGAATCCCCTGACCTCAAGGACAGTTTGCTG
[A,G]
TAAGCAAACTAGGAGAATAAAACGTTTATATAGAAAGAGGAAAATCCATGGCACTCATAC
TCCTACCTCCAACCCCATGCTCATGGCAGACATCACTAATCAATCACAGTACTTTTGATC
ACTGAAACCCTTATGTGGTCTTAGAATCTTTAACAGGACACTCCAAGAAATCACTGCTGA
CAGCCAACTGATTTGTGAGATAAGGTCTCCATGCATCTGGATCTTCCATAGAACTGATAG
TTGCACAGCATAAAATGGTGAGGGTGGGGCCATTGTGGGTTGAGCCACCAAGGAAGGCCA (SEQ ID NO:22)

8661 TGTTTCGTGACAAAGTGTTCAGAACAGCCCCCACTCCACCCTGGATAATTATCCACAGAG
ACCAAGGGAAAAACACAACCAGAAAAGTCCACACATACATCCAGGGCAAGTTGCAAGAAA
GTGACTCAGTCAGACAGAGTGAGTGGTTGTATCCTCACAACCAAACTATTATAGAGACAA
AAATTTGATAAATTCAAGCACCAATTTTGTTCACGACATTGTATAGGTTTCATGAATCCC
CTGACCTCAAGGACAGTTTGCTGATAAGCAAACTAGGAGAATAAAACGTTTATATAGAAA
[G,A]
AGGAAAATCCATGGCACTCATACTCCTACCTCCAACCCCATGCTCATGGCAGACATCACT
AATCAATCACAGTACTTTTGATCACTGAAACCCTTATGTGGTCTTAGAATCTTTAACAGG
ACACTCCAAGAAATCACTGCTGACAGCCAACTGATTTGTGAGATAAGGTCTCCATGCATC
TGGATCTTCCATAGAACTGATAGTTGCACAGCATAAAATGGTGAGGGTGGGGCCATTGTG
GGTTGAGCCACCAAGGAAGGCCATCCAGGCCTGGATGGGCCAGAACAAAGGTACAGATGA (SEQ ID NO:23)

11754 GCTCCTGGAGCTGGTGGGAGACAAGATTAAGCAAACCTCCCCTGACATGTATCCCTTTGA
CCCCAAGCTCTGCCTCCTCCCTGACCACCCATGCCCTTTCCTTTAACTTCTCAAACAGAT
ACCAGGGCCTAAACTGCTTTACCTCCCCTCCTACTGAGTCAGGTTAGGTGGTGGGAGGTC
ACCCATTTCCGAGTTAAACCAATGCAATATGAGTAAAACAAAGTCATGTGGGTATGTCTG
GGGTAGAGAGAGGGGTAGCAAGTTCATGTGTCCTCCTTGGTCACATATCTCCCAAAGCTC
[T,C]
GATCCCTGCCATGGGAAGTGGACAGGAAACATGAGGTCATGACCTGCAGGCATCTTTACT
GCAGCTCTGCCGGCCTGGAGGGGGAGAGGGGGAGGAAGAAGTATGCGCTGCACATTTCTG
AGGCTACTGCATTTGCTTTCAAGGCAGAAATCTTGCTCTGAGCAGTCAGCGGCTCCAGTT
TGGGCCCGATAAGGAAGTTCTCCGTGGCCTCCCTCAGGCAGAGCAGGGAGGAGGCTGACA
TTGCCAGTCTCTTCTGGGGCCCAAGGCAGGTTGCAGGAGATCCAATCCCATAGACAGCTC (SEQ ID NO:24)

11836 GACCACCCATGCCCTTTCCTTTAACTTCTCAAACAGATACCAGGGCCTAAACTGCTTTAC
CTCCCCTCCTACTGAGTCAGGTTAGGTGGTGGGAGGTCACCCATTTCCGAGTTAAACCAA

FIGURE 3G

TGCAATATGAGTAAAACAAAGTCATGTGGGTATGTCTGGGGTAGAGAGAGGGGTAGCAAG
TTCATGTGTCCTCCTTGGTCACATATCTCCCAAAGCTCTGATCCCTGCCATGGGAAGTGG
ACAGGAAACATGAGGTCATGACCTGCAGGCATCTTTACTGCAGCTCTGCCGGCCTGGAGG
[A,G]
GGAGAGGGGGAGGAAGAAGTATGCGCTGCACATTTCTGAGGCTACTGCATTTGCTTTCAA
GGCAGAAATCTTGCTCTGAGCAGTCAGCGGCTCCAGTTTGGGCCCGATAAGGAAGTTCTC
CGTGGCCTCCCTCAGGCAGAGCAGGGAGGAGGCTGACATTGCCAGTCTCTTCTGGGGCCC
AAGGCAGGTTGCAGGAGATCCAATCCCATAGACAGCTCTGGGCCTCTTGCATTTGAGTTT
TTCAGAATTAAACTGCAGTATTTTGGAAAGCACATCCTGTCCACTGTTTCTTTGAAGTGA (SEQ ID NO:25)

FIGURE 3H

SEQUENCE LISTING

<160> NUMBER OF SEQ ID NOS: 4

<210> SEQ ID NO 1
<211> LENGTH: 2674
<212> TYPE: DNA
<213> ORGANISM: Human

<400> SEQUENCE: 1
ttcgcctgcg ggccggcact gctcacctct cgtccaggga catgacgggc acgccaggcg 60
ccgttgccac ccgggatggc gaggccccg agcgctcccc gccctgcagt ccgagctacg 120
acctcacggg caaggtgatg cttctgggag acacaggcgt cggcaaaaca tgtttcctga 180
tccaattcaa agacggggcc ttcctgtccg gaaccttcat agccaccgtc ggcatagact 240
tcaggaacaa ggtggtgact gtggatggcg tgagagtgaa gctgcagatc tgggacaccg 300
ctgggcagga acggttccga agcgtcaccc atgcttatta cagagatgct caggccttgc 360
ttctgctgta tgacatcacc aacaaatctt ctttcgacaa catcagggcc tggctcactg 420
agattcatga gtatgcccag agggacgtgg tgatcatgct gctaggcaac aaggcggata 480
tgagcagcga aagagtgatc cgttccgaag acggagagac cttggccagg gagtacggtg 540
ttcccttcct ggagaccagc gccaagactg gcatgaatgt ggagttagcc tttctggcca 600
tcgccaagga actgaaatac cgggccgggc atcaggcgga tgagcccagc ttccagatcc 660
gagactatgt agagtcccag aagaagcgct ccagctgctg ctccttcatg tgaatcccag 720
ggggcagaga ggaggctctg gaggcacaca ggatgcagcc ttccccctcc caggcctggc 780
ttattccaag aggctgagcc aatggggaga aagatggagg actcactgca cagccgcttc 840
ctagcaggga gctatactcc aactcctact tgagttcctg cggtctcccc gcatccacag 900
ggagggtaaa acacttagct tttattttaa tagtacataa tttaatacca aaaaaggcgc 960
ctggatcccc aaaaaaccga ggctgggagc tagtggccct tttgctttct aggacttggg 1020
gggccggccc tccctcctaa gcataacaaa ggtggtgttg ctccagctca gccccagggg 1080
acacagatgc actttggggg tgagggcagg taatgactcc atcgcaccct cagttcagct 1140
ggacagaggc tcaggtgacc ccagccttca ctgtctcccg ctctccagga gcttatcttc 1200
gccccatctc ccaaataagt gggcccttgt gctgtgagga agaccaaagc ctcagggaag 1260
ataagagata tggagatggg agggggagga caaggggcag agagtagggt ctagctggct 1320
atctctggcc ttactaacac ccccctggag gcatgcccct tttctccagc acacaagcac 1380
attggggcac ctggaaatat tggttccagg ctcctgttct ctggacttca gatcctgggg 1440
gagcccctcc cccccctgaa tccctggctt agctaccttc ctgcctgtgc acctaaaaac 1500
ctcaggtcag aactaggaaa agagttttgt ttttattttt ttgaaatgga gtctcgttct 1560
gtcgcccagg ctgaggtgca gtagtgcaat ctccgctcac tacaacctcc actccctggg 1620
gctcaagcga tcctcccacc tcagccgccg aagtagctgg gactataggt gtgtaccatc 1680

-continued

```
acacctggct aatttttgta ttttttgtag acacagggtt tcgccatgtt gcccaggctg   1740

gtcttgaatt cctgagctca agcaacctgc cggcctcggc ctcccaaagt actgggatta   1800

cacgcagaag gcaccatgcc caggctagat gtgtcttatc ccaatccttt ggcaggcatg   1860

cagctccaca ggcgatttct tcaagcagct gaagtgttta gccctcctgg gttaagagcc   1920

agataaggag aaatcccttt cctaggtttg gaatgtgttg tgaaaaaaaa gagaaatccc   1980

tggctcctgg agctggtggg agacaagatt aagcaaacct cccctgacat gtatcccttt   2040

gaccccaagc tctgcctcct ccctgaccac ccatgccctt tcctttaact tctcaaacag   2100

ataccagggc ctaaactgct ttacctcccc tcctactgag tcaggttagg tggtgggagg   2160

tcacccattt ccgagttaaa ccaatgcaat atgagtaaaa caaagtcatg tgggtatgtc   2220

tggggtagag agaggggtag caagttcatg tgtcctcctt ggtcacatat ctcccaaagc   2280

tctgatccct gccatgggaa gtggacagga aacatgaggt catgacctgc aggcatcttt   2340

actgcagctc tgccggcctg gagggggaga gggggaggaa gaagtatgcg ctgcacattt   2400

ctgaggctac tgcatttgct ttcaaggcag aaatcttgct ctgagcagtc agcggctcca   2460

gtttgggccc gataaggaag ttctccgtgg cctccctcag gcagagcagg gaggaggctg   2520

acattgccag tctcttctgg ggcccaaggc aggttgcagg agatccaatc ccatagacag   2580

ctctgggcct cttgcatttg agtttttcag aattaaactg cagtattttg gaaagcaaaa   2640

aaaaaaaaaa aaaaaaaaaa aaaaaaaaaa aaaa                               2674
```

```
<210> SEQ ID NO 2
<211> LENGTH: 223
<212> TYPE: PRT
<213> ORGANISM: Human

<400> SEQUENCE: 2

Met Thr Gly Thr Pro Gly Ala Val Ala Thr Arg Asp Gly Glu Ala Pro
 1               5                  10                  15

Glu Arg Ser Pro Pro Cys Ser Pro Ser Tyr Asp Leu Thr Gly Lys Val
            20                  25                  30

Met Leu Leu Gly Asp Thr Gly Val Gly Lys Thr Cys Phe Leu Ile Gln
        35                  40                  45

Phe Lys Asp Gly Ala Phe Leu Ser Gly Thr Phe Ile Ala Thr Val Gly
    50                  55                  60

Ile Asp Phe Arg Asn Lys Val Val Thr Val Asp Gly Val Arg Val Lys
65                  70                  75                  80

Leu Gln Ile Trp Asp Thr Ala Gly Gln Glu Arg Phe Arg Ser Val Thr
                85                  90                  95

His Ala Tyr Tyr Arg Asp Ala Gln Ala Leu Leu Leu Leu Tyr Asp Ile
            100                 105                 110

Thr Asn Lys Ser Ser Phe Asp Asn Ile Arg Ala Trp Leu Thr Glu Ile
        115                 120                 125

His Glu Tyr Ala Gln Arg Asp Val Val Ile Met Leu Leu Gly Asn Lys
    130                 135                 140

Ala Asp Met Ser Ser Glu Arg Val Ile Arg Ser Glu Asp Gly Glu Thr
145                 150                 155                 160

Leu Ala Arg Glu Tyr Gly Val Pro Phe Leu Glu Thr Ser Ala Lys Thr
                165                 170                 175

Gly Met Asn Val Glu Leu Ala Phe Leu Ala Ile Ala Lys Glu Leu Lys
            180                 185                 190

Tyr Arg Ala Gly His Gln Ala Asp Glu Pro Ser Phe Gln Ile Arg Asp
```

-continued

```
        195                 200                 205

Tyr Val Glu Ser Gln Lys Lys Arg Ser Ser Cys Cys Ser Phe Met
    210                 215                 220


<210> SEQ ID NO 3
<211> LENGTH: 13182
<212> TYPE: DNA
<213> ORGANISM: Human
<220> FEATURE:
<221> NAME/KEY: misc_feature
<222> LOCATION: (1)...(13182)
<223> OTHER INFORMATION: n = A,T,C or G

<400> SEQUENCE: 3

aggggagaga aaagaccgca taccaggcca ggtgcggtgg ctcacgcttg taatcccagc      60

aatttggaag gccaaggcag gcgtatcgcc tgaggtcagc agttccaaac cagcctgtcc     120

aacatggtga agttctctac taagaataca aaaattaccc aggcgtggtg gcgtgcacct     180

gtagtcccag ctgctccaga ggctgaggca ggagaattgc ttgaacctgg gaggcagagg     240

ctgcaatgcg ccaagatccc gccactgcac tccagcctgg gcgacagagt gagactccgt     300

ctccgggagc ccacggcatt gagcaaacct cggcattatt tgcagcaaga gcctctggca     360

tccaaatagc aaccaacacc acgcctctgt agtgtgctgc gcagcctcca cactccagtc     420

tgaggctccc tgtttgagtc ccgccctatg cccagctgag gttatagcac gctcacctcc     480

agaagaggta acccaagctc tttactctac tggagatcac ctctgtcccc actctgggcg     540

cttctcccag ctgacagaaa atacctccag ctgatgtcag aaaatacagg gctggaggct     600

ggcgtacaaa gtcagtcccc acaggcctat ggtggcccat aagccacgtc taccccctgct     660

cctcacctcc acacctaagt taagaattgc aggccgggcg cagtggctca cgcctgtaat     720

cccagcactt tgggaggctg aggtgggcgg accgcctgag gtcaggaatt tgagaccagc     780

ttggccaaca tggcaaaacc ccgtctctac taaaaataca aaaagaaaaa atagccgggc     840

ctgatgtcgc gcacctgtaa tcccagctac tccgggagac tgaggcggga gtatagcttg     900

aacccgggaa gcaaaggttg cagtgaggcg agatcgcacc actgcactcc aggctgggcg     960

acagagtgag actctgtctg aaaaaaaaaa aaagtgcagg taccccctctc cagctctccc    1020

ctccctacac atccctcaaa ccgtcccgct gtaatgcacc cgccctgttc cttggtaact    1080

tgaagctgct tatagaatgt ggagatgggg gtaattgaaa ggtcggccca ggccacagag    1140

cccctgagct ctgctaccgg caaccccagc tgcactcccc actctctgtc accaggagct    1200

gccgggtgcc tgggatatcc tggcagctct gctcaaaatg atctacgact tcatgaattt    1260

atttggctcc tcctcggggc cagggtgagt gtcatgggtt aataaggccg gccccgcctt    1320

caggagcggt ccactgggag atgtgtgctg cgcagccctc ttgcgaaagc tctcccctgg    1380

tgggacattc tgggcacaac caacaggccg ggggaaatga gaggtgatcc atactaaagg    1440

gtcaaagtcc ccgcaccagg cagaggcccc aaaacaccgc agcgtacatg tgctgcaagg    1500

cgagtacggg ttggtaaaca aaactatatt cagatgagct cgggccgggt gacttaacag    1560

atgaggaagt gtctcggggc catcggcgga ggcgcagccc aggggtcccc agctccccgc    1620

ctcgccacct ggggacagcc cacggcccgg ggctcgggcg ccgcctgctg tcgcggtgcg    1680

cagcgactac gggaactctt ccgcagcaga cggggtcccc gcggcccgct cccccagggg    1740

caagcaagcg accacagggg accggtcccg gggctggatg tggctcatgt ccgaagcgca    1800

cggagccgag ccggtgttgc tcagggaggc tgcccgcccc ttcacgcaga ccctgcggct    1860
```

-continued

```
ctgcgtgccc tcagggaaca gcaaggtccg agccggtgtc gtcgaggggg cgacgggacg   1920
gagggaggag cctgaggggt cccggtcgag ggaggggagg agtgggcggg gcgggggtgg   1980
gggccgttcc cgcgctctcc ttcgcctgcg ggccggcact gctcacctct cgtccaggga   2040
catgacgggc acgccaggcg ccgttgccac ccgggatggc gaggccccg agcgctcccc   2100
gccctgcagt ccgagctacg acctcacggg caaggtgggt gggcctcttc cgtgagaccc   2160
ccgccctcct cggcgctagc cccttcctgg ctgcgtctgg gttggactca gcccttcccc   2220
caggcagctg cgtctcccag aggagggagg gagagagggt caggacacag cctctggggc   2280
cgtcccaagc tctaggtgtc tctgctggct tggtgggggc gggtcgcgga agatcgcaaa   2340
aactgagtga tccccccgcc ggccccaact cagttctctt ctgccacact ctggcaaata   2400
tgagcccccg ggagcccatg cttcttggtg agggttaagc gcgcaactct cggggctcag   2460
gctgggaagg gctgggagat ggggaccgaa cggagactcg gagaggacgt cccctgctgg   2520
cagaggaact ggcgttaatg ccattttccg agctaagctc ttagttgaga tctgacatcc   2580
aggtttaagg cctgatgtcc cccagctgct cccctcccat tccacccgct ggaggcactg   2640
cctcccacct tcctccctgc agtcggaagc cgctcctccc agaaggatgt tgccagccgg   2700
cctgcaggtc acttgggaat ttttcgaacc tgagaaagat ttcagtggtt ggtctttcgc   2760
atcccgcact tgagagagct ccagggctgc tctctggggc ttgctccctc tacaggggtg   2820
tcctgtatgg aaacaggtag ggacagcagt ggactggtct gtcgccttcc atctgtgtcc   2880
ttggagtgag cgggtaccag aaactgaaag aactgctgag ggagcctaga gcttccactc   2940
ttcctctgca gggttgggga tggagtgagg gctgtcctgg attccgctgc atggccttga   3000
aggagacctg cctctctctg ggcctcggtt tcctccccga caccagggct caccccttgct   3060
gggagcctca gcctccaccc cagtgtttcg gggggaagcca ccctgcaagt catccgccca   3120
gagccgttga gataggcgtc ctgtgtgggc ttgtggcagg aaatgggccc ctgcaccctc   3180
ggagaggagg agctgctgtt ggccaggccc caggctgagg gggactgcct gaccttgttg   3240
ccctgcaaac cagctgggtt gtttgcctag gaggtggcca ggctaggcag ctgtttgtgt   3300
ttggtggaat caccgagctg ggtgggtagc tggcatcgtt tgctcaaggc agctgtgatc   3360
tgtaaagtac acaaagactg gccctccctc cctccttcct gctccagggc tgggacccag   3420
gagccaggga ggagtgcagg ctccagaaag ctcctatccc ccacccccttc atctgttccc   3480
tggccaagcg gcattggccg gagagttggt ccccagcctc cccgggcctg ccccagggga   3540
gtgagtccag gaccctctga gaaagcctgg caggagctcc ttggaccaga ctaggggtga   3600
tgtggcccac aggcagacag ttcccaccct gggccactct tccctgggtc ttaggtgatt   3660
caccacgatg atgggcccta gccattaaca gactctagaa atacctcaaa gacattatcc   3720
ctcctccttc tacccactat ggaaaccatg ccacagaaag gttaaggaat cttcctaaag   3780
tcacacagta ggccatttac aaatcaagac ccatccttca taccccttct gctcagccac   3840
ccctgcctct ccaccagagt taactaatgc cagtacccca tgcccacaac aggaatgcct   3900
ttgggctcca ctgtcaattt cagagcctca aaaataattc aaacctagtc cctgcttaac   3960
ccattaagcc acctaaccag cagctgggaa attccagcat tggatctaga cccctgttat   4020
ccaagattgg agaacagtgg gacaaagtgc tcctctccac cattcctgcg tgtccctggg   4080
gaagatgagc agagcagagc cagacagtaa aggagagggc cacgcccccct ccacaggtta   4140
cctccttggt actcctgccc gcactaccca cagcaacccc gggatgccga tctgcagcca   4200
catgtcccat gtgggaggtt tctgctgaaa gaacttccaa ctacacatct ccccacttca   4260
```

-continued

```
gtataaattt caaccttccc taattcatgc aacctttttt tttttttttt ttttttgaga   4320
cagagtgtcg ctctgtcacc gaggctggag ttcagtgatg caatctcggc tcactgcaac   4380
ctctacctcc tgggttcaag ctattctcct gtctccgcct cccaagtaac tgggactaca   4440
ggcgtgtgcc accactcctg gctagttttt tgtattttta gtagagatgg ggtttcacct   4500
tgttggtcag gctggtctca aactcccaac tcaggtgatc cgtccacttg ggcacccaaa   4560
atgnnnnnnn nnnnnnnnnn nnnnnnnnnn nnnnnnnnnn nnnnnnnnnn nnnnnnnnnn   4620
nnnnnnnnnn nnnnnnnnnn nnnnnnnnnn nnnnnnnnnn nnnnnnnnnn nnnnnnnnnn   4680
nnnnnnnnnn nnnnnnnnnn nnnnnnnnnn nnnnnnnnnn ttcaagtacc agcctggcca   4740
acatggtaga aaccccgtct ctactaaaaa taaaaaatta gccaggcgag gtggtgcatg   4800
cctataatcc cagctactca ggtaggctga ggcaggagaa tcatttaaac ctgggaggtg   4860
gaggttgtgg tgagccaaga tctcgccatt gcactccagc ctgggcaaca agagcaaaac   4920
tccgtctcaa aaaaaaaaag aaagaaagaa agaaagaaac ttccaaataa atgttgtgac   4980
acaaaaaaaa aaacccaaac aatattcatt atagagtatg caaatgacca tgccccaccc   5040
ccagcagatt ctgatagact cccttgggtg ggaatccttg tccaatatat tgacacttcc   5100
ctttcctgtc agtatagccc agcccatgcg tgtactcacg agcggacgat ggatgacaca   5160
agtacacaga gggacggaat ccctgcatgg tgtggctatg ggcaaatgtg gccactgtct   5220
agattgtgca aatgtggtgg ttctctgggg ccacagagca cacttgggga cctgttcatg   5280
gtgaggtctc aactccggcc tctaggaact tgaatgagga caggagggtc agagggagag   5340
cctaggaggc tgagccaagg agcgtggaga ggagagacag ggtgaaggtg gcggctggct   5400
ttctggaagc aggtggcctt tggtgcggtc agcattcgtg ccagccccct cttctctgat   5460
cctctccatg tgtctctctc ctggaatccc agaagctgcc cctgactccc cattaactgc   5520
ctctgcccct acccccctagg tgatgcttct gggagacaca ggcgtcggca aaacatgttt   5580
cctgatccaa ttcaaagacg gggccttcct gtccggaacc ttcatagcca ccgtcggcat   5640
agacttcagg gtgaggtggc tgcaggcact tgcttccagc agagagccag ggctgtggct   5700
caggcatggg ggggttgccc ccaccttgct caccctggct cccagggact cccgaggctc   5760
atgcctggag ggcacacaac ccgctccccc aagaccacag aggtggccgg gtcaaaggag   5820
actgggcaag gttggctcct tgcccaacta taggatgcaa aaaaatgaga ctgagtcttc   5880
gattccagct ccattcctgg gggacttctc ccaagcagag cagccgcagg cacggcataa   5940
gctgaatatc ttggcccaca gagcccctgc tcattgctct cctacctggg cccctttgga   6000
aaggcctcaa aggtcaatca gtctttctgg agttcccaga aagcacagcc ctgcactggg   6060
tttaagagct gggcttgggc caggcatggt ggctcttgcc tgtattccca gcactttggg   6120
aggccgaagc ggtcagatca caaggtcagg agtttgagac cagcctggcc aacatggtga   6180
aaccccgtct ctactaaaaa tacaaaaatt agccaggtgt agtggcacgc tcctgcagtc   6240
ccagctactc gggaggctga ggcaggagaa tcgctcaaat ccgggtggtg gaggttgcag   6300
tgagctgaga tcgcgccact gcactccagc ctgggcaaca aagtgagact gcgtctcaga   6360
aaaaaaaaaa aaaaaagagc tgggctggcc atgttgggag acagcagctc accagggacc   6420
ctccctctca ccttgacgac tccatcttac aaatctgcat cagggatgct agacgctgca   6480
cacctgaagt gttcaataga gaaaaggtct caccctggca ggtggggctc tacagcttca   6540
agcaggcaga aagcgaacac ttccttcact agagaattag tgggcagcta aagaaaaggt   6600
```

-continued

```
gctgctgcag atgtagcctc aggtccccag gatgcaggca aacaccccat ctccaggggc   6660
tcggtcacag tcccaaggct aggctccagg agagggagac cgaagtgggg aaagggcagg   6720
gcctccagca gcaaccagcc ctccagccct gggctgcctg atccctggag agagccagga   6780
tgtttctcag gctcctcttg ccctgctgtt gtgagaaggc agttacagtc ctcagaaggg   6840
acgactccac agtggaggtg tctgggtatg gggttcctgc tgccctgatg gtatgatctg   6900
gctggagacg gttctggggc tcactgcacc cactctaggc ctggagaggg aacaagagag   6960
gacgtctgca gagctgagga gccacatgac tcctgccctc ccatcctctg ccttttctc   7020
tttcagaaca aggtggtgac tgtggatggc gtgagagtga agctgcaggt gagaccagag   7080
gctggagttg gggagggagg atggaggacc tgcccttcct tctcaccctg aaccacagga   7140
ggcctgcagc cctgccctcc gcctggggca atttcctgtg ggcccacggg gaggaaatgg   7200
cttttgttta tttgacatct gcagaaaaag cagttcccag gcaccctctc atctatgaac   7260
agcagctcca aatgccttca gacaagctta gcctccatcc atctcctccc cagttgccag   7320
ggctttatct gctcttagga gattggacat ccccaacccc tgagctaggg gagaggagaa   7380
gattcttttt ttttctttc ttttcttttt tttttgaga tggagtctcg ctctgtcgcc   7440
caggctggag tgcagtggca caatctcggc tcactgcaac ctctgcctcc caggtttaag   7500
agattctcct gcctcagcct cctgagtagc tgagactaca ggtgcatgcc accacacctg   7560
gctaattttt tgtattttta gtagagacgg ggtttcactg tgttagccag gatggtctgg   7620
atctcctgac ctcgtgatcc gcctgcctcg gcctcccaaa gtgctgggat tacaggtgta   7680
agccaccgcg ctcggctgag gagatgattt tgaacgagct tgagaaatca gtaactgcta   7740
ctgtccaggt cattggatgc tcaggggctc atgagaacct aaagaagaaa acagccccac   7800
cttcccacag atatctcata caacaaagca ggcctgctcc acccagcaca ttccttgcac   7860
ctgcctcctt ctgaccattt ctccatccca tcccttccca gatctgggac accgctgggc   7920
aggaacggtt ccgaagcgtc acccatgctt attacagaga tgctcagggt gagtccctcg   7980
caccctccaa cccctacccc agccccttgg tagcatccgt gctgctgcct aagtcccctc   8040
tgtgatcctc tcccctccag ccttgcttct gctgtatgac atcaccaaca aatcttcttt   8100
cgacaacatc agggtaggtc ctcccttccc ctgactccca cccataagca gccaaggcaa   8160
ggtctatgca ggctggggtt gcttcctgcc ctgtggaaag cgggtggagc gtggagtcct   8220
cctgccttct gaaaaacacc tacttgtgac tcagaagtca tatctgctgc tttgtatttg   8280
gtggccatgt gggcatgaag gccaagcagg ctgttgtgac cctgtgccac ctgcatagcc   8340
ctcactgtga ttcacgagtg tgtttcgtga caaagtgttc agaacagccc ccactccacc   8400
ctggataatt atccacagag accaagggaa aaacacaacc agaaaagtcc acacatacat   8460
ccagggcaag ttgcaagaaa gtgactcagt cagacagagt gagtggttgt atcctcacaa   8520
ccaaactatt atagagacaa aaatttgata aattcaagca ccaattttgt tcacgacatt   8580
gtataggttt catgaatccc ctgacctcaa ggacagtttg ctgataagca aactaggaga   8640
ataaaacgtt tatatagaaa gaggaaaatc catggcactc atactcctac ctccaacccc   8700
atgctcatgg cagacatcac taatcaatca cagtactttt gatcactgaa acccttatgt   8760
ggtcttagaa tctttaacag gacactccaa gaaatcactg ctgacagcca actgatttgt   8820
gagataaggt ctccatgcat ctggatcttc catagaactg atagttgcac agcataaaat   8880
ggtgagggtg gggccattgt gggttgagcc accaaggaag gccatccagg cctggatggg   8940
ccagaacaaa ggtacagatg agagaacgca cagggtatcg tgttcaaggt agtgagtaac   9000
```

-continued

```
tgaggatagt caaacggagc agaagaagaa aggggcagca ggaggaagag aatgccagtc   9060
tcgcacgccc tctcccacag gcctggctca ctgagattca tgagtatgcc cagagggacg   9120
tggtgatcat gctgctaggc aacaaggtga gtggctccgg ggcagggtca gcccagccct   9180
gcacttcctc agccctagcc ggccccataa ccacccaaga acagttatct aggcatcctt   9240
cctgaaaagg actctgcagc ctccagctca ggggtcagac atatctggag gcttctgccc   9300
atcccatctg ccccttccag ggaaagtcca agttgttgcc tgagaaatca aggggtgccc   9360
agttctcagc ccccattaga gcagagtgaa cagggtccca ggtcaggggc taagagtgca   9420
aagggttagc cccaactgct gtcctattcc aagacccttt accaaaggtg agatcccaga   9480
gctgggagct acactgggca gaaaccctgg ccccaggcca atcacacctg cctgcagtcc   9540
cttgggccac cagcagaggg caggcaacgc ctgcttctgg ggcaaaatat gggcccgctg   9600
gggcggaggc ctccttcccc agagtgaccc atttgggctt gacaggcgga tatgagcagc   9660
gaaagagtga tccgttccga agacggagag accttggcca gggtaagtga ttgtctgtgg   9720
gacagggtga agggtggggg caacccgacg ctggccctga ggacactctc tcccgggcag   9780
gagtacggtg ttcccttcct ggagaccagc gccaagactg gcatgaatgt ggagttagcc   9840
tttctggcca tcgccaagtg agagctgggc agggaaggga agtgtgcggg gcagggcggc   9900
acactccagg aatccagtag ggcccggccc ctggcccagc ccctggacac acctgcattc   9960
tgcaggctga ggtccatttg ctctgggagc actgggccac tgggagaggg gagggggcgg  10020
ctcagctcct caccccagcc cagcccagcc cagcccagcc cattgtctct tcttcaaggg  10080
aactgaaata ccgggccggg catcaggcgg atgagcccag cttccagatc cgagactatg  10140
tagagtccca gaagaagcgc tccagctgct gctccttcat gtgaatccca gggggcagag  10200
aggaggctct ggaggcacac aggatgcagc cttccccctc ccaggcctgg cttattccaa  10260
gaggctgagc caatggggag aaagatggag gactcactgc acagccgctt cctagcaggg  10320
agctatactc caactcctac ttgagttcct gcggtctccc cgcatccaca gggagggtaa  10380
aacacttagc ttttatttta atagtacata atttaatacc aaaaaaggcg cctggatccc  10440
caaaaaaccg aggctgggag ctagtggccc ttttgctttc taggacttgg ggggccggcc  10500
ctccctccta agcataacaa aggtggtgtt gctccagctc agccccaggg gacacagatg  10560
cactttgggg gtgagggcag gtaatgactc catcgcaccc tcagttcagc tggacagagg  10620
ctcaggtgac cccagccttc actgtctccc gctctccagg agcttatctt cgccccatct  10680
cccaaataag tgggcccttg tgctgtgagg aagaccaaag cctcagggaa gataagagat  10740
atggagatgg gagggggagg acaaggggca gagagtaggg tctagctggc tatctctggc  10800
cttactaaca ccccccctgga ggcatgcccc ttttctccag cacacaagca cattggggca  10860
cctggaaata ttggttccag gctcctgttc tctggacttc agatcctggg ggagcccctc  10920
ccccccctga atccctggct tagctacctt cctgcctgtg cacctaaaaa cctcaggtca  10980
gaactaggaa aagagttttg tttttatttt tttgaaatgg agtctcgttc tgtcgcccag  11040
gctgaggtgc agtagtgcaa tctccgctca ctacaacctc cactccctgg ggctcaagcg  11100
atcctcccac ctcagccgcc gaagtagctg ggactatagg tgtgtaccat cacacctggc  11160
taatttttgt atttttttgta gacacagggt ttcgccatgt tgcccaggct ggtcttgaat  11220
tcctgagctc aagcaacctg ccggcctcgg cctcccaaag tactgggatt acacgcagaa  11280
ggcaccatgc ccaggctaga tgtgtcttat cccaatcctt tggcaggcat gcagctccac  11340
```

-continued

```
aggcgatttc ttcaagcagc tgaagtgttt agccctcctg ggttaagagc cagataagga  11400

gaaatccctt tcctaggttt ggaatgtgtt gtgaaaaaaa agagaaatcc ctggctcctg  11460

gagctggtgg gagacaagat taagcaaacc tcccctgaca tgtatccctt tgaccccaag  11520

ctctgcctcc tccctgacca cccatgccct ttcctttaac ttctcaaaca gataccaggg  11580

cctaaactgc tttacctccc ctcctactga gtcaggttag gtggtgggag gtcacccatt  11640

tccgagttaa accaatgcaa tatgagtaaa acaaagtcat gtgggtatgt ctggggtaga  11700

gagaggggta gcaagttcat gtgtcctcct tggtcacata tctcccaaag ctctgatccc  11760

tgccatggga agtggacagg aaacatgagg tcatgacctg caggcatctt tactgcagct  11820

ctgccggcct ggagggggag agggggagga agaagtatgc gctgcacatt tctgaggcta  11880

ctgcatttgc tttcaaggca gaaatcttgc tctgagcagt cagcggctcc agtttgggcc  11940

cgataaggaa gttctccgtg gcctccctca ggcagagcag ggaggaggct gacattgcca  12000

gtctcttctg ggcccaagg caggttgcag gagatccaat cccatagaca gctctgggcc  12060

tcttgcattt gagtttttca gaattaaact gcagtatttt ggaaagcaca tcctgtccac  12120

tgtttctttg aagtgagtgg gggggggggg tcttgttgaa ggaattgtca ttcactgcca  12180

aaatcattcc atcctccttc ctcagtgtct gtcctcagat ggtcagctcc ccgctcaaca  12240

gactgtctcc cgcctctgtg accagcctct ctttggcaag agggagctag aaggctttac  12300

agtcctaatc atttttctgt tggaaaaaaa aaaaaaaaac caaggctcct ttccctgtgg  12360

cgtgtaccca gaggttgatt acctgagtct gtcctgcctc tccccacccc acctccctag  12420

ccaaacgctg ctgccaaagc ccacgctatt gccctagatg gcctgtcttc agcgggctgc  12480

ccctcgaggt cccaggctct ccgcggagcc ctcaccttcc cagcagggat cagaacctgc  12540

actcctctat gcgagtcctg ggacagcaca aagtggatta gggttagggt tcccacaaac  12600

ggaaaaatgt tattcaaaca actctgtagg gtccgaggag gccctccgtc ttaattctcg  12660

agactgaccg gccctcgctg ccccgagcgg gagcagttgc cccggcaaca gccgctccct  12720

ctcaactgga gctgcaccca ggctttggct aaaggctgtt aaaacgttgg ccaggtgcgg  12780

aggctcacgt ctgtaatccc agggcggatc acctgaggtc aggagtttga aaccatcctg  12840

gccaacatgg cgaaatttcg tctctactaa aaatacaaaa attagcgggg cgtggtggtg  12900

cgcgcctgta accccagctg ctcgggaggc tgaggcaggg gaatcgcttg aacccgggag  12960

gcggaggttg cagtgatccg agatcgcgcc acggcagtcc agcctgggcg acagagcgag  13020

actccgtctc aaaaaaaaaa aaaaaagtta gggtccttta cccgagggcc ggctttcctc  13080

actccccgcc acaggtaggg gaaaccaggc cggagccggc gggcccaccc gcccagaacc  13140

gggaattcgg cgagccccgc ccctgccacc ccagcgccgg cc                      13182
```

```
<210> SEQ ID NO 4
<211> LENGTH: 223
<212> TYPE: PRT
<213> ORGANISM: Mus musculus

<400> SEQUENCE: 4

Met Thr Gly Thr Pro Gly Ala Ala Thr Ala Gly Asp Gly Glu Ala Pro
 1               5                  10                  15

Glu Arg Ser Pro Pro Phe Ser Pro Asn Tyr Asp Leu Thr Gly Lys Val
            20                  25                  30

Met Leu Leu Gly Asp Ser Gly Val Gly Lys Thr Cys Phe Leu Ile Gln
        35                  40                  45
```

-continued

```
Phe Lys Asp Gly Ala Phe Leu Ser Gly Thr Phe Ile Ala Thr Val Gly
    50                  55                  60

Ile Asp Phe Arg Asn Lys Val Val Thr Val Asp Gly Ala Arg Val Lys
65                  70                  75                  80

Leu Gln Ile Trp Asp Thr Ala Gly Gln Glu Arg Phe Arg Ser Val Thr
                85                  90                  95

His Ala Tyr Tyr Arg Asp Ala Gln Ala Leu Leu Leu Leu Tyr Asp Ile
            100                 105                 110

Thr Asn Gln Ser Ser Phe Asp Asn Ile Arg Ala Trp Leu Thr Glu Ile
        115                 120                 125

His Glu Tyr Ala Gln Arg Asp Val Val Ile Met Leu Leu Gly Asn Lys
    130                 135                 140

Ala Asp Val Ser Ser Glu Arg Val Ile Arg Ser Glu Asp Gly Glu Thr
145                 150                 155                 160

Leu Ala Arg Glu Tyr Gly Val Pro Phe Met Glu Thr Ser Ala Lys Thr
                165                 170                 175

Gly Met Asn Val Glu Leu Ala Phe Leu Ala Ile Ala Lys Glu Leu Lys
            180                 185                 190

Tyr Arg Ala Gly Arg Gln Pro Asp Glu Pro Ser Phe Gln Ile Arg Asp
        195                 200                 205

Tyr Val Glu Ser Gln Lys Lys Arg Ser Ser Cys Cys Ser Phe Val
    210                 215                 220
```

ISOLATED HUMAN RAS-LIKE PROTEINS, NUCLEIC ACID MOLECULES ENCODING THESE HUMAN RAS-LIKE PROTEINS, AND USES THEREOF

FIELD OF THE INVENTION

The present invention is in the field of Ras-like proteins that are related to the Rab GTPase subfamily, recombinant DNA molecules and protein production. The present invention specifically provides novel Ras-like protein polypeptides and proteins and nucleic acid molecules encoding such peptide and protein molecules, all of which are useful in the development of human therapeutics and diagnostic compositions and methods.

BACKGROUND OF THE INVENTION

Ras-like proteins, particularly members of the Rab GTPase subfamilies, are a major target for drug action and development. Accordingly, it is valuable to the field of pharmaceutical development to identify and characterize previously unknown members of this subfamily of Ras-like proteins. The present invention advances the state of the art by providing a previously unidentified human Ras-like proteins that have homology to members of the Rab GTPase subfamilies.

Ras Protein

Ras proteins are small regulatory GTP-binding proteins, or small G proteins, which belong to the Ras protein superfamily. They are monomeric GTPases, but their GTPase activity is very slow (less than one GTP molecule per minute).

Ras proteins are key relays in the signal-transducing cascade induced by the binding of a ligand to specific receptors such as receptor tyrosine kinases (RTKs), since they trigger the MAP kinase cascade. The ligand can be a growth factor (epidermal growth factor (EGF), platelet-derived growth factor (PDGF), insulin, an interleukin (IL), granulocyte colony-stimulating factor (G-CSF), granulocyte/macrophage colony-stimulating factor (GM-CSF).

Ras proteins contain sequences highly conserved during evolution. Their tertiary structure includes ten loops connecting six strands of beta-sheet and five alpha helices.

In mammalians, there are four Ras proteins, which are encoded by Ha-ras, N-ras, Ki-rasA and Ki-rasB genes. They are composed of about 170 residues and have a relative molecular mass of 21 kD. Ras proteins contain covalently attached modified lipids allowing these proteins to bind to the plasma membrane. Ha-Ras has a C-terminal farnesyl group, a C-terminal palmitoyl group and a N-terminal myristoyl group. In Ki-Ras(B), a C-terminal polylysine domain replaces the palmitoyl group.

Ras proteins alternate between an inactive form bound to GDP and an active form bound to GTP. Their activation results from reactions induced by a guanine nucleotide-exchange factor (GEF). Their inactivation results from reactions catalyzed by a GTPase-activating protein (GAP).

When a Ras protein is activated by a GEF such as a Sos protein, the N-terminal region of a serine/threonine kinase, called “Raf protein”, can bind to Ras protein. The C-terminal region of the activated Raf thus formed binds to another protein, MEK, and phosphorylates it on both specific tyrosine and serine residues. Active MEK phosphorylates and activates, in turn, a MAP kinase (ERK1 or ERK2), which is also a serine/threonine kinase. This phosphorylation occurs on both specific tyrosine and threonine residues of MAP kinase.

MAP kinase phosphorylates many different proteins, especially nuclear transcription factors (TFs) that regulate expression of many genes during cell proliferation and differentiation.

Recent researches suggest that, in mammalians, phosphatidyl inositol 3'-kinase (PI3-kinase) might be a target of Ras protein, instead of Raf protein. In certain mutations, the translation of ras genes may produce oncogenic Ras proteins.

Ras-Like Protein

Guanine nucleotide-binding proteins (GTP-binding proteins, or G proteins) participate in a wide range of regulatory functions including metabolism, growth, differentiation, signal transduction, cytoskeletal organization, and intracellular vesicle transport and secretion. These proteins control diverse sets of regulatory pathways in response to hormones, growth factors, neuromodulators, or other signaling molecules. When these molecules bind to transmembrane receptors, signals are propagated to effector molecules by intracellular signal transducing proteins. Many of these signal-transducing proteins are members of the Ras superfamily.

The Ras superfamily is a class of low molecular weight (LMW) GTP-binding proteins that consist of 21–30 kDa polypeptides. These proteins regulate cell growth, cell cycle control, protein secretion, and intracellular vesicle interaction. In particular, the LMW GTP-binding proteins activate cellular proteins by transducing mitogenic signals involved in various cell functions in response to extracellular signals from receptors (Tavitian, A. (1995) C. R. Seances Soc. Biol. Fil. 189:7–12). During this process, the hydrolysis of GTP acts as an energy source as well as an on-off switch for the GTPase activity of the LMW GTP-binding proteins.

The Ras superfamily is comprised of five subfamilies: Ras, Rho, Ran, Rab, and ADP-ribosylation factor (ARF). Specifically, Ras genes are essential in the control of cell proliferation. Mutations in Ras genes have been associated with cancer. Rho proteins control signal transduction in the process of linking receptors of growth factors to actin polymerization that is necessary for cell division. Rab proteins control the translocation of vesicles to and from membranes for protein localization, protein processing, and secretion. Ran proteins are localized to the cell nucleus and play a key role in nuclear protein import, control of DNA synthesis, and cell-cycle progression. ARF and ARF-like proteins participate in a wide variety of cellular functions including vesicle trafficking, exocrine secretion, regulation of phospholipase activity, and endocytosis.

Despite their sequence variations, all five subfamilies of the Ras superfamily share conserved structural features. Four conserved sequence regions (motifs I–IV) have been studied in the LMW GTP-binding proteins. Motif I is the most variable but has the conserved sequence, GXXXXGK (SEQ ID NO:26). The lysine residue is essential in interacting with the .beta.- and .gamnma.-phosphates of GTP. Motif II, III, and IV contain highly conserved sequences of DTAGQ (SEQ ID NO:27), NKXD (SEQ ID NO:28), and EXSAX (SEQ ID NO:29), respectively. Specifically, Motif II regulates the binding of gamma-phosphate of GTP; Motif III regulates the binding of GTP; and Motif IV regulates the guanine base of GTP. Most of the membrane-bound LMW GTP-binding proteins generally require a carboxy terminal isoprenyl group for membrane association and biological activity. The isoprenyl group is added posttranslationally through recognition of a terminal cysteine residue alone or a terminal cysteine-aliphatic amino acid-aliphatic amino acid-any amino acid (CAAX; SEQ ID NO:30) motif. Additional membrane-binding energy is often provided by either internal palmitoylation or a carboxy terminal cluster of basic amino acids. The LMW GTP-binding proteins also have a variable effector region, located between motifs I and II, which is characterized as the interaction site for guanine nucleotide exchange factors (GEFs) or GTPase-activating proteins (GAPs). GEFs induce the release of GDP from the active form of the G protein, whereas GAPs interact with the inactive form by stimulating the GTPase activity of the G protein.

The ARF subfamily has at least 15 distinct members encompassing both ARF and ARF-like proteins. ARF proteins identified to date exhibit high structural similarity and ADP-ribosylation enhancing activity. In contrast, several ARF-like proteins lack ADP-ribosylation enhancing activity and bind GTP differently. An example of ARF-like proteins is a rat protein, ARL184. ARL184 has been shown to have a molecular weight of 22 kDa and four functional GTP-binding sites (Icard-Liepkalns, C. et al. (1997) Eur. J. Biochem. 246: 388–393). ARLI 84 is active in both the cytosol and the Golgi apparatus and is closely associated with acetylcholine release, suggesting that ARL184 is a potential regulatory protein associated with Ca.sup.2+-dependent release of acetylcholine.

A number of Rho GTP-binding proteins have been identified in plasma membrane and cytoplasm. These include RhoA, B and C, and D, rhoG, rac 1 and 2, G25K-A and B, and TC10 (Hall, A. Ct al. (1993) Philos. Trans. R. Soc. Lond. (Biol.) 340:267–271). All Rho proteins have a CAAX (SEO ID NO:30) motif that binds a prenyl group and either a palmitoylation site or a basic amino acid-rich region, suggesting their role in membrane-associated functions. In particular, RhoD is a protein that functions in early endosome motility and distribution by inducing rearrangement of actin cytoskeleton and cell surface (Murphy, C. et al. (1996) Nature 384:427–432). During cell adhesion, the Rho proteins are essential for triggering focal complex assembly and integrin-dependent signal transduction (Hotchin, N. A. and Hall, A. (1995) J. Cell Biol. 131:1857–1865).

The Ras subfamily proteins already indicated supra are essential in transducing signals from receptor tyrosine kinases (RTKs) to a series of serine/threonine kinases which control cell growth and differentiation. Mutant Ras proteins, which bind but cannot hydrolyze GTP, are permanently activated and cause continuous cell proliferation or cancer. TC21, a Ras-like protein, is found to be highly expressed in a human teratocarcinoma cell line (Drivas, G. T. et al. (1990) Mol. Cell. Biol. 10:1793–1798). Rin and Rit are characterized as membrane-binding, Ras-like proteins without the lipid-binding CAAX (SEO ID NO:30) motif and carboxy terminal cysteine (Lee, C.-H. J. et al. (1996) J. Neurosci. 16: 6784–6794). Further, Rin is shown to localize in neurons and have calcium-dependant calmodulin-binding activity.

Rab GTPases

The novel human protein, and encoding gene, provided by the present invention is a novel protein of the Ras family and shows the greatest degree of similarity to Rab GTPases in general and Rab37 in particular.

GTPases play important roles in a wide variety of cell functions such as signal transduction, cytoskeletal organization, and membrane trafficking. Rab GTPases are particularly important for regulating cellular membrane dynamics by modulating the activity of effector proteins that then regulate vesicle trafficking. Rab37 is a Rab GTPase that is expressed in the MC-9 mast cell line and bone marrow mast cells. Rab37 shares 74% sequence identity with Rab26 and 47% sequence identity with Rab8. The Rab8 GTPase plays important roles in Golgi to plasma membrane vesicle trafficking. Studies have suggested that Rab37 plays an important role in mast cell degranulation. Thus, Rab37, as well as other novel human Rab GTPases, are valuable as potential therapeutic targets for the development of allergy treatments (Masuda et al, *FEBS Lett* Mar. 17, 2000; 470).

The discovery of new human Ras-like proteins and the polynucleotides that encode them satisfies a need in the art by providing new compositions that are useful in the diagnosis, prevention, and treatment of inflammation and disorders associated with cell proliferation and apoptosis.

SUMMARY OF THE INVENTION

The present invention is based in part on the identification of amino acid sequences of human Ras-like protein polypeptides and proteins that are related to the Rab GTPase Ras-like protein subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate Ras-like protein activity in cells and tissues that express the Ras-like protein. Experimental data as provided in FIG. 1 indicates expression in humans in prostate, brain, T-cells from T-cell leukemia, leukopheresis, and leukocytes.

DESCRIPTION OF THE FIGURE SHEETS

FIG. 1 provides the nucleotide sequence of a cDNA molecule that encodes the Ras-like protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in humans in prostate, brain, T-cells from T-cell leukemia, leukopheresis, and leukocytes.

FIG. 2 provides the predicted amino acid sequence of the Ras-like protein of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the Ras-like protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs were identified at 10 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a Ras-like protein or part of a Ras-like protein and are related to the Rab GTPase subfamily. Utilizing these sequences, additional genomic sequences were assembled and transcript and/or cDNA sequences were isolated and characterized. Based on this analysis, the present invention provides amino acid sequences of human Ras-like protein polypeptides that are related to the Rab GTPase subfamily, nucleic acid sequences in the form of transcript sequences, cDNA sequences and/or genomic sequences that encode these Ras-like protein polypeptide, nucleic acid variation (allelic information), tissue distribution of expression, and information about the closest art known protein/peptide/domain that has structural or sequence homology to the Ras-like protein of the present invention.

In addition to being previously unknown, the peptides that are provided in the present invention are selected based on their ability to be used for the development of commercially important products and services. Specifically, the present peptides are selected based on homology and/or structural relatedness to known Ras-like proteins of the Rab GTPase subfamily and the expression pattern observed. Experimental data as provided in FIG. 1 indicates expression in humans in prostate, brain, T-cells from T-cell leukemia, leukopheresis, and leukocytes. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known Rab GTPase family or subfamily of Ras-like proteins.

Specific Embodiments

Peptide Molecules

The present invention provides nucleic acid sequences that encode protein molecules that have been identified as being members of the Ras-like protein family and are related to the Rab GTPase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the Ras-like proteins or peptides of the present invention, Ras-like proteins or peptides, or peptides/proteins of the present invention.

The present invention provides isolated peptide and protein molecules that consist of, consist essentially of, or comprise the amino acid sequences of the Ras-like protein polypeptide disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components.

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the Ras-like protein polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated Ras-like protein polypeptide can be purified from cells that naturally express it, purified from cells that have been altered to express it (recombinant), or synthesized using known protein synthesis methods. Experimental data as provided in FIG. 1 indicates expression in humans in prostate, brain, T-cells from T-cell leukemia, leukopheresis, and leukocytes. For example, a nucleic acid molecule encoding the Ras-like protein polypeptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the Ras-like protein polypeptide of the present invention are the naturally occurring mature proteins. A brief description of how various types of these proteins can be made/isolated is provided below.

The Ras-like protein polypeptides of the present invention can be attached to heterologous sequences to form chimeric or fusion proteins. Such chimeric and fusion proteins comprise a Ras-like protein polypeptide operatively linked to a heterologous protein having an amino acid sequence not substantially homologous to the Ras-like protein polypeptide. "Operatively linked" indicates that the Ras-like protein polypeptide and the heterologous protein are fused in-frame. The heterologous protein can be fused to the N-terminus or C-terminus of the Ras-like protein polypeptide.

In some uses, the fusion protein does not affect the activity of the Ras-like protein polypeptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant Ras-like protein polypeptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology,* 1992). Moreover, many expression vectors are commercially available that already encode a fusion moiety (e.g., a GST protein). A Ras-like protein polypeptide-encoding nucleic acid can be cloned into such an expression vector such that the fusion moiety is linked in-frame to the Ras-like protein polypeptide.

As mentioned above, the present invention also provides and enables obvious variants of the amino acid sequence of the peptides of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art know techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the Ras-like protein polypeptides of the present invention. The degree of homology/identity present will be based primarily on whether the peptide is a functional variant or non-functional variant, the amount of divergence present in the paralog family, and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, 40%, 50%, 60%, 70%, 80%, or 90% or more of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A.M., ed., Oxford University Press, New York, 1988; *Biocomputing: Informatics and Genome Projects*, Smith, D. W., ed., Academic Press, New York, 1993; *Computer Analysis of Sequence Data. Part* 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 199 1). In a preferred embodiment, the percent identity between two amino acid sequences is determined using the Needlernan and Wunsch (*J. Mol. Biol.* (48):444–453 (1970)) algorithm which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, word length=12 to obtain nucleotide sequences homologous to the nucleic acid molecules of the invention. BLAST protein searches can be performed with the XBLAST program, score=50, word length=3, to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the Ras-like protein polypeptides of the present invention as well as being encoded by the same genetic locus as the Ras-like protein polypeptide provided herein. The gene encoding the novel Ras-like protein of the present invention is located on a genome component that has been mapped to human chromosome 17 (as indicated in FIG. 3), which is supported by multiple lines of evidence, such as STS and BAC map data.

Allelic variants of a Ras-like protein polypeptide can readily be identified as being a human protein having a high degree (significant) of sequence homology/identity to at least a portion of the Ras-like protein polypeptide as well as being encoded by the same genetic locus as the Ras-like protein polypeptide provided herein. Genetic locus can readily be determined based on the genomic information provided in FIG. 3, such as the genomic sequence mapped to the reference human. The gene encoding the novel Ras-like protein of the present invention is located on a genome component that has been mapped to human chromosome 17 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a Ras-like protein polypeptide encoding nucleic acid molecule under stringent conditions as more fully described below.

FIG. 3 provides information on SNPs that have been found in the gene encoding the Ras-like protein of the present invention. SNPs were identified at 10 different nucleotide positions. Some of these SNPs that are located outside the ORF and in introns may affect gene transcription.

Paralogs of a Ras-like protein polypeptide can readily be identified as having some degree of significant sequence homology/identity to at least a portion of the Ras-like protein polypeptide, as being encoded by a gene from humans, and as having similar activity or function. Two proteins will typically be considered paralogs when the amino acid sequences are typically at least about 40–50%, 50–60%, and more typically at least about 60–70% or more homologous through a given region or domain. Such paralogs will be encoded by a nucleic acid sequence that will hybridize to a Ras-like protein polypeptide encoding nucleic acid molecule under moderate to stringent conditions as more fully described below.

Orthologs of a Ras-like protein polypeptide can readily be identified as having some degree of significant sequence homology/identity to at least a portion of the Ras-like protein polypeptide as well as being encoded by a gene from another organism. Preferred orthologs will be isolated from mammals, preferably primates, for the development of human therapeutic targets and agents. Such orthologs will be encoded by a nucleic acid sequence that will hybridize to a Ras-like protein polypeptide encoding nucleic acid molecule under moderate to stringent conditions, as more fully described below, depending on the degree of relatedness of the two organisms yielding the proteins.

Non-naturally occurring variants of the Ras-like protein polypeptides of the present invention can readily be generated using recombinant techniques. Such variants include, but are not limited to deletions, additions and substitutions in the amino acid sequence of the Ras-like protein polypeptide. For example, one class of substitutions is conserved amino acid substitutions. Such substitutions are those that substitute a given amino acid in a Ras-like protein polypeptide by another amino acid of like characteristics. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg, replacements among the aromatic residues Phe, Tyr, and the like. Guidance concerning which amino acid changes are likely to be phenotypically silent are found in Bowie et al., *Science* 247:1306–1310 (1990).

Variant Ras-like protein polypeptides can be fully functional or can lack function in one or more activities. Fully functional variants typically contain only conservative variations or variations in non-critical residues or in non-critical regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)). The latter procedure introduces single alanine mutations at every residue in the molecule. The resulting mutant molecules are then tested for biological activity such as receptor binding or in vitro proliferative activity. Sites that are critical for ligand-receptor binding can also be determined by structural analysis such as crystallography, nuclear magnetic resonance, or photoaffinity labeling (Smith et al, *J. Mol. Biol.* 224:899–904 (1992); de Vos et al. *Science* 255:306–312 (1992)).

The present invention further provides fragments of the Ras-like protein polypeptides, in addition to proteins and peptides that comprise and consist of such fragments. Particularly those comprising the residues identified in FIG. 2. The fragments to which the invention pertains, however, are not to be construed as encompassing fragments that have been disclosed publicly prior to the present invention.

As used herein, a fragment comprises at least 8, 10, 12, 14, 16 or more contiguous amino acid residues from a Ras-like protein polypeptide. Such fragments can be chosen based on the ability to retain one or more of the biological activities of the Ras-like protein polypeptide, or can be chosen for the ability to perform a function, e.g., act as an immunogen. Particularly important fragments are biologically active fragments, peptides that are, for example about 8 or more amino acids in length. Such fragments will typically comprise a domain or motif of the Ras-like protein polypeptide, e.g., active site. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE, HMMer, eMOTIF, etc.). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in Ras-like protein polypeptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Posttranslational Covalent Modification of proteins,* B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the Ras-like protein polypeptides of the present invention also encompass derivatives or analogs in which a substituted amino acid residue is not one encoded by the genetic code, in which a substituent group is included, in which the mature Ras-like protein polypeptide is fused with another compound, such as a compound to increase the half-life of the Ras-like protein polypeptide (for example, polyethylene glycol), or in which the additional amino acids are fused to the mature Ras-like protein polypeptide, such as a leader or secretory sequence or a sequence for purification of the mature Ras-like protein polypeptide, or a pro-protein sequence.

Protein/Peptide Uses

The proteins of the present invention can be used in assays to determine the biological activity of the protein, including in a panel of multiple proteins for high-throughput screening; to raise antibodies or to elicit another immune response; as a reagent (including the labeled reagent) in assays designed to quantitatively determine levels of the protein (or its ligand or receptor) in biological fluids; and as markers for tissues in which the corresponding protein is preferentially expressed (either constitutively or at a particular stage of tissue differentiation or development or in a disease state). Where the protein binds or potentially binds to another protein (such as, for example, in a receptor-ligand interaction), the protein can be used to identify the binding partner so as to develop a system to identify inhibitors of the binding interaction. Any or all of these research utilities are capable of being developed into reagent grade or kit format for commercialization as research products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, Ras-like proteins isolated from humans and their human/mammalian orthologs serve as targets for identifying agents for use in mammalian therapeutic applications, e.g. a human drug, particularly in modulating a biological or pathological response in a cell or tissue that expresses the Ras-like protein. Experimental data as provided in FIG. 1 indicates that Ras-like proteins of the present invention are expressed in humans in prostate, brain, T-cells from T-cell leukemia, and leukopheresis, as indicated by virtual northern blot analysis. In addition, PCR-based tissue screening panels indicate expression in leukocytes. A large percentage of pharmaceutical agents are being developed that modulate the activity of Ras-like proteins, particularly members of the Rab GTPase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in prostate, brain, T-cells from T-cell leukemia, leukopheresis, and leukocytes. Such uses can readily be determined using the information provided herein, that which is known in the art, and routine experimentation.

The proteins of the present invention (including variants and fragments that may have been disclosed prior to the present invention) are useful for biological assays related to Ras-like proteins that are related to members of the Rab GTPase subfamily. Such assays involve any of the known Ras-like protein functions or activities or properties useful for diagnosis and treatment of Ras-like protein-related conditions that are specific for the subfamily of Ras-like proteins that the one of the present invention belongs to, particularly in cells and tissues that express the Ras-like protein. Experimental data as provided in FIG. 1 indicates that Ras-like proteins of the present invention are expressed in humans in prostate, brain, T-cells from T-cell leukemia, and leukopheresis, as indicated by virtual northern blot analysis. In addition, PCR-based tissue screening panels indicate expression in leukocytes.

The proteins of the present invention are also useful in drug screening assays, in cell-based or cell-free systems. Cell-based systems can be native, i.e., cells that normally express the Ras-like protein, as a biopsy or expanded in cell culture. Experimental data as provided in FIG. 1 indicates expression in humans in prostate, brain, T-cells from T-cell leukemia, leukopheresis, and leukocytes. In an alternate embodiment, cell-based assays involve recombinant host cells expressing the Ras-like protein.

The polypeptides can be used to identify compounds that modulate Ras-like protein activity. Both the Ras-like protein of the present invention and appropriate variants and fragments can be used in high-throughput screens to assay candidate compounds for the ability to bind to the Ras-like protein. These compounds can be further screened against a functional Ras-like protein to determine the effect of the compound on the Ras-like protein activity. Further, these compounds can be tested in animal or invertebrate systems to determine activity/effectiveness. Compounds can be identified that activate (agonist) or inactivate (antagonist) the Ras-like protein to a desired degree.

Therefore, in one embodiment, Rab GTPase or a fragment or derivative thereof may be administered to a subject to prevent or treat a disorder associated with an increase in apoptosis. Such disorders include, but are not limited to, AIDS and other infectious or genetic immunodeficiencies, neurodegenerative diseases such as Alzheimer's disease, Parkinson's disease, amyotrophic lateral sclerosis, retinitis pigmentosa, and cerebellar degeneration, myelodysplastic syndromes such as aplastic anemia, ischemic injuries such as myocardial infarction, stroke, and reperfusion injury, toxin-induced diseases such as alcohol-induced liver damage, cirrhosis, and lathyrism, wasting diseases such as cachexia, viral infections such as those caused by hepatitis B and C, and osteoporosis.

In another embodiment, a pharmaceutical composition comprising Rab GTPase may be administered to a subject to prevent or treat a disorder associated with increased apoptosis including, but not limited to, those listed above.

In still another embodiment, an agonist which is specific for Rab GTPase may be administered to prevent or treat a disorder associated with increased apoptosis including, but not limited to, those listed above.

In a further embodiment, a vector capable of expressing Rab GTPase, or a fragment or a derivative thereof, may be used to prevent or treat a disorder associated with increased apoptosis including, but not limited to, those listed above.

In cancer, where Rab GTPase promotes cell proliferation, it is desirable to decrease its activity. Therefore, in one embodiment, an antagonist of Rab GTPase may be administered to a subject to prevent or treat cancer including, but not limited to, adenocarcinoma, leukemia, lymphoma, melanoma, myeloma, sarcoma, and teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody specific for Rab GTPase may be used directly as an antagonist, or indirectly as a targeting or delivery mechanism for bringing a pharmaceutical agent to cells or tissue which express Rab GTPase.

In another embodiment, a vector expressing the complement of the polynucleotide encoding Rab GTPase may be administered to a subject to prevent or treat a cancer including, but not limited to, the types of cancer listed above.

In inflammation, where Rab GTPase promotes cell proliferation, it is desirable to decrease its activity. Therefore, in one embodiment, an antagonist of Rab GTPase may be administered to a subject to prevent or treat an inflammation. Disorders associated with inflammation include, but are not limited to, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjogren's syndrome, and autoimmune thyroiditis; complications of cancer, hemodialysis, extracorporeal circulation; viral, bacterial, fungal, parasitic, protozoal, and helminthic infections and trauma. In one aspect, an antibody specific for Rab GTPase may be used directly as an antagonist, or indirectly as a targeting or delivery mechanism for bringing a pharmaceutical agent to cells or tissue which express Rab GTPase.

Further, the Ras-like protein polypeptides can be used to screen a compound for the ability to stimulate or inhibit interaction between the Ras-like protein and a molecule that normally interacts with the Ras-like protein, e.g. a ligand or a component of the signal pathway that the Ras-like protein normally interacts. Such assays typically include the steps of combining the Ras-like protein with a candidate compound under conditions that allow the Ras-like protein, or fragment, to interact with the target molecule, and to detect the formation of a complex between the protein and the target or to detect the biochemical consequence of the interaction with the Ras-like protein and the target, such as any of the associated effects of signal transduction.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries). (Hodgson, Bio/technology, Sep. 10, 1992 (9);973–80).

One candidate compound is a soluble fragment of the Ras-like protein that competes for ligand binding. Other candidate compounds include mutant Ras-like proteins or appropriate fragments containing mutations that affect Ras-like protein function and thus compete for ligand. Accordingly, a fragment that competes for ligand, for example with a higher affinity, or a fragment that binds ligand but does not allow release, is within the scope of the invention.

The invention further includes other end point assays to identify compounds that modulate (stimulate or inhibit) Ras-like protein activity. The assays typically involve an assay of events in the Ras-like protein mediated signal transduction pathway that indicate Ras-like protein activity. Thus, the phosphorylation of a protein/ligand target, the expression of genes that are up- or down-regulated in response to the Ras-like protein dependent signal cascade can be assayed. In one embodiment, the regulatory region of such genes can be operably linked to a marker that is easily detectable, such as luciferase. Alternatively, phosphorylation of the Ras-like protein, or a Ras-like protein target, could also be measured.

Any of the biological or biochemical functions mediated by the Ras-like protein can be used as an endpoint assay. These include all of the biochemical or biochemical/biological events described herein, in the references cited herein, incorporated by reference for these endpoint assay targets, and other functions known to those of ordinary skill in the art.

Binding and/or activating compounds can also be screened by using chimeric Ras-like proteins in which any of the protein's domains, or parts thereof, can be replaced by heterologous domains or subregions. Accordingly, a different set of signal transduction components is available as an end-point assay for activation. This allows for assays to be performed in other than the specific host cell from which the Ras-like protein is derived.

The Ras-like protein polypeptide of the present invention is also useful in competition binding assays in methods designed to discover compounds that interact with the Ras-like protein. Thus, a compound is exposed to a Ras-like protein polypeptide under conditions that allow the compound to bind or to otherwise interact with the polypeptide. Soluble Ras-like protein polypeptide is also added to the mixture. If the test compound interacts with the soluble Ras-like protein polypeptide, it decreases the amount of complex formed or activity from the Ras-like protein target. This type of assay is particularly useful in cases in which compounds are sought that interact with specific regions of the Ras-like protein. Thus, the soluble polypeptide that competes with the target Ras-like protein region is designed to contain peptide sequences corresponding to the region of interest.

To perform cell free drug screening assays, it is sometimes desirable to immobilize either the Ras-like protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase/15625 fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of Ras-like protein-binding protein found in the bead fraction quantitated from the gel using standard electrophoretic techniques. For example, either the polypeptide or its target molecule can be immobilized utilizing conjugation of biotin and streptavidin with techniques well known in the art. Alternatively, antibodies reactive with the protein but which do not interfere with binding of the protein to its target molecule can be derivatized to the wells of the plate, and the protein trapped in the wells by antibody conjugation. Preparations of a Ras-like protein-binding protein and a candidate compound are incubated in the Ras-like protein-presenting wells and the amount of complex trapped in the well can be quantitated. Methods for detecting such complexes, in addition to those described above for the GST-immobilized complexes, include immunodetection of complexes using antibodies reactive with the Ras-like protein target molecule, or which are reactive with Ras-like protein and compete with the target molecule, as well as enzyme-linked assays which rely on detecting an enzymatic activity associated with the target molecule.

Agents that modulate one of the Ras-like proteins of the present invention can be identified using one or more of the above assays, alone or in combination. It is generally preferable to use a cell-based or cell free system first and then confirm activity in an animal/insect model system. Such model systems are well known in the art and can readily be employed in this context.

Modulators of Ras-like protein activity identified according to these drug screening assays can be used to treat a subject with a disorder mediated by the Ras-like protein associated pathway, by treating cells that express the Ras-like protein. Experimental data as provided in FIG. 1 indicates expression in humans in prostate, brain, T-cells from T-cell leukemia, leukopheresis, and leukocytes. These methods of treatment include the steps of administering the modulators of protein activity in a pharmaceutical composition as described herein, to a subject in need of such treatment.

In yet another aspect of the invention, the Ras-like proteins can be used as "bait proteins" in a two-hybrid assay or three-hybrid assay (see, e.g., U.S. Pat. No. 5,283,317; Zervos et al., *Cell* 72:223–232 (1993); Madura et al., *J. Biol. Chem.* 268:12046–12054 (1993); Bartel et al., *Biotechniques* 14:920–924 (1993); Iwabuchi et al., *Oncogene* 8:1693–1696 (1993); and Brent WO94/10300), to identify other proteins that bind to or interact with the Ras-like protein and are involved in Ras-like protein activity. Such Ras-like protein-binding proteins are also likely to be involved in the propagation of signals by the Ras-like proteins or Ras-like protein targets as, for example, downstream elements of a Ras-like protein-mediated signaling pathway, e.g., a pain signaling pathway. Alternatively, such Ras-like protein-binding proteins are likely to be Ras-like protein inhibitors.

The two-hybrid system is based on the modular nature of most transcription factors, which consist of separable DNA-binding and activation domains. Briefly, the assay utilizes two different DNA constructs. In one construct, the gene that codes for a Ras-like protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a Ras-like protein-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the Ras-like protein.

This invention further pertains to novel agents identified by the above-described screening assays. Accordingly, it is within the scope of this invention to further use an agent identified as described herein in an appropriate animal model. For example, an agent identified as described herein (e.g., a Ras-like protein modulating agent, an antisense Ras-like protein nucleic acid molecule, a Ras-like protein-specific antibody, or a Ras-like protein-binding partner) can be used in an animal or insect model to determine the efficacy, toxicity, or side effects of treatment with such an agent. Alternatively, an agent identified as described herein can be used in an animal or insect model to determine the mechanism of action of such an agent. Furthermore, this invention pertains to uses of novel agents identified by the above-described screening assays for treatments as described herein.

The Ras-like proteins of the present invention are also useful to provide a target for diagnosing a disease or predisposition to a disease mediated by the peptide, Accordingly, the invention provides methods for detecting the presence, or levels of, the protein (or encoding mRNA) in a cell, tissue, or organism. Experimental data as provided in FIG. 1 indicates expression in humans in prostate, brain, T-cells from T-cell leukemia, leukopheresis, and leukocytes. The method involves contacting a biological sample with a compound capable of interacting with the receptor protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells, and fluids present within a subject.

The peptides also are useful to provide a target for diagnosing a disease or predisposition to a disease mediated by the peptide, Accordingly, the invention provides methods for detecting the presence, or levels of, the protein in a cell, tissue, or organism. The method involves contacting a biological sample with a compound capable of interacting with the receptor protein such that the interaction can be detected.

The peptides of the present invention also provide targets for diagnosing active disease, or predisposition to a disease, in a patient having a variant peptide. Thus, the peptide can be isolated from a biological sample and assayed for the presence of a genetic mutation that results in translation of an aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered receptor activity in cell-based or cell-free assay, alteration in ligand or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations, and immunofluorescence using a detection reagents, such as an antibody or protein binding agent. Alternatively, the peptide can be detected in vivo in a subject by introducing into the subject a labeled anti-peptide antibody. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the receptor protein in which one or more of the receptor functions in one population is different from those in another population. The peptides thus allow a target to ascertain a genetic predisposition that can affect treatment modality. Thus, in a ligand-based treatment, polymorphism may give rise to amino terminal extracellular domains and/or other ligand-binding regions that are more or less active in ligand binding, and receptor activation. Accordingly, ligand dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in prostate, brain, T-cells from T-cell leukemia, leukopheresis, and leukocytes. Accordingly, methods for treatment include the use of the Ras-like protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or $F(ab')_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the Ras-like proteins. Antibodies can be prepared from any region of the peptide as described herein. However, preferred regions will include those involved in function/activity and/or receptor/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection of an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$, or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that Ras-like proteins of the present invention are expressed in humans in prostate, brain, T-cells from T-cell leukemia, and leukopheresis, as indicated by virtual northern blot analysis. In addition, PCR-based tissue screening panels indicate expression in leukocytes. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development. Antibody detection of circulating fragments of the full-length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in prostate, brain, T-cells from T-cell leukemia, leukopheresis, and leukocytes. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in prostate, brain, T-cells from T-cell leukemia, leukopheresis, and leukocytes. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in prostate, brain, T-cells from T-cell leukemia, leukopheresis, and leukocytes. Thus, where a specific protein has been correlated with expression in a specific tissue, antibodies that are specific for this protein can be used to identify a tissue type.

The antibodies are also useful for inhibiting protein function, for example, blocking the binding of the Ras-like protein to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use.

Nucleic Acid Molecules

The present invention further provides isolated nucleic acid molecules that encode a Ras-like protein polypeptide of the present invention. Such nucleic acid molecules will consist of, consist essentially of, or comprise a nucleotide sequence that encodes one of the Ras-like protein polypeptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule. The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

Full-length genes may be cloned from known sequence using any one of a number of methods known in the art. For example, a method which employs XL-PCR (Perkin-Elmer, Foster City, Calif.) to amplify long pieces of DNA may be used. Other methods for obtaining full-length sequences are well known in the art.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life, or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the Ras-like protein polypeptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding, and stability of mRNA. In addition, the nucleic acid molecule may be fused to a marker sequence encoding, for example, a peptide that facilitates purification.

Isolated nucleic acid molecules can be in the form of RNA, such as mRNA, or in the form of DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention and that encode obvious variants of the Ras-like proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or whole organisms. Accordingly, as discussed above, the variants can contain nucleotide substitutions, deletions inversions, and/or insertions. Variation can occur in either or both the coding and non-coding regions. The variations can produce both conservative and non-conservative amino acid substitutions.

The present invention further provides non-coding fragments of the nucleic acid molecules provided in the FIGS. 1 and 3. Preferred non-coding fragments include, but are not limited to, promoter sequences, enhancer sequences, gene modulating sequences, and gene termination sequences. Such fragments are useful in controlling heterologous gene expression and in developing screens to identify gene-modulating agents.

A fragment comprises a contiguous nucleotide sequence greater than 12 or more nucleotides. Further, a fragment could be at least 30, 40, 50, 100 250, or 500 nucleotides in length. The length of the fragment will be based on its intended use. For example, the fragment can encode epitope-bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50, or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. The gene encoding the novel Ras-like protein of the present invention is located on a genome component that has been mapped to human chromosome 17 (as indicated in FIG. 3), which is supported by multiple lines of evidence, such as STS and BAC map data.

FIG. 3 provides information on SNPs that have been found in the gene encoding the Ras-like protein of the present invention. SNPs were identified at 10 different nucleotide positions. Some of these SNPs that are located outside the ORF and in introns may affect gene transcription.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45 C., followed by one or more washes in 0.2×SSC, 0.1% SDS at 50–65° C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at 10 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as those, which may encompass fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene encoding the novel Ras-like protein of the present invention is located on a genome component that has been mapped to human chromosome 17 (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for constructing host cells expressing a part, or all, of the nucleic acid molecules and peptides. Moreover, the nucleic acid molecules are useful for constructing transgenic animals wherein a homolog of the nucleic acid molecule has been "knocked-out" of the animal's genome.

The nucleic acid molecules are also useful for constructing transgenic animals expressing all, or a part, of the nucleic acid molecules and peptides.

The nucleic acid molecules are also useful for making vectors that express part, or all, of the peptides.

The nucleic acid molecules are also useful as hybridization probes for determining the presence, level, form, and distribution of nucleic acid expression. Experimental data as provided in FIG. 1 indicates that Ras-like proteins of the present invention are expressed in humans in prostate, brain, T-cells from T-cell leukemia, and leukopheresis, as indicated by virtual northern blot analysis. In addition, PCR-based tissue screening panels indicate expression in leukocytes. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in Ras-like protein expression relative to normal results.

In vitro techniques for detection of mRNA include Northern hybridizations and in situ hybridizations. In vitro techniques for detecting DNA include Southern hybridizations and in situ hybridization.

Probes can be used as a part of a diagnostic test kit for identifying cells or tissues that express a Ras-like protein, such as by measuring a level of a receptor-encoding nucleic acid in a sample of cells from a subject e.g., mRNA or genomic DNA, or determining if a receptor gene has been mutated. Experimental data as provided in FIG. 1 indicates that Ras-like proteins of the present invention are expressed in humans in prostate, brain, T-cells from T-cell leukemia, and leukopheresis, as indicated by virtual northern blot analysis. In addition, PCR-based tissue screening panels indicate expression in leukocytes.

Nucleic acid expression assays are useful for drug screening to identify compounds that modulate Ras-like protein nucleic acid expression.

The invention thus provides a method for identifying a compound that can be used to treat a disorder associated with nucleic acid expression of the Ras-like protein gene, particularly biological and pathological processes that are mediated by the Ras-like protein in cells and tissues that express it. Experimental data as provided in FIG. 1 indicates expression in humans in prostate, brain, T-cells from T-cell leukemia, leukopheresis, and leukocytes. The method typically includes assaying the ability of the compound to modulate the expression of the Ras-like protein nucleic acid and thus identifying a compound that can be used to treat a disorder characterized by undesired Ras-like protein nucleic acid expression. The assays can be performed in cell-based and cell-free systems. Cell-based assays include cells naturally expressing the Ras-like protein nucleic acid or recombinant cells genetically engineered to express specific nucleic acid sequences.

The assay for Ras-like protein nucleic acid expression can involve direct assay of nucleic acid levels, such as mRNA levels, or on collateral compounds involved in the signal pathway. Further, the expression of genes that are up- or down-regulated in response to the Ras-like protein signal pathway can also be assayed. In this embodiment the regulatory regions of these genes can be operably linked to a reporter gene such as luciferase.

Thus, modulators of Ras-like protein gene expression can be identified in a method wherein a cell is contacted with a candidate compound and the expression of mRNA determined. The level of expression of Ras-like protein mRNA in the presence of the candidate compound is compared to the level of expression of Ras-like protein mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate Ras-like protein nucleic acid expression in cells and tissues that express the Ras-like protein. Experimental data as provided in FIG. 1 indicates that Ras-like proteins of the present invention are expressed in humans in prostate, brain, T-cells from T-cell leukemia, and leukopheresis, as indicated by virtual northern blot analysis. In addition, PCR-based tissue screening panels indicate expression in leukocytes. Modulation includes both up-regulation (i.e. activation or agonization) or down-regulation (suppression or antagonization) of nucleic acid expression.

Alternatively, a modulator for Ras-like protein nucleic acid expression can be a small molecule or drug identified using the screening assays described herein as long as the drug or small molecule inhibits the Ras-like protein nucleic acid expression in the cells and tissues that express the protein. Experimental data as provided in FIG. 1 indicates expression in humans in prostate, brain, T-cells from T-cell leukemia, leukopheresis, and leukocytes.

The nucleic acid molecules are also useful for monitoring the effectiveness of modulating compounds on the expression or activity of the Ras-like protein gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in Ras-like protein nucleic acid, and particularly in qualitative changes that lead to pathology. The nucleic acid molecules can be used to detect mutations in Ras-like protein genes and gene expression products such as mRNA. The nucleic acid molecules can be used as hybridization probes to detect naturally occurring genetic mutations in the Ras-like protein gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns, or changes in gene copy number, such as amplification. Detection of a mutated form of the Ras-like protein gene associated with a dysfunction provides a diagnostic tool for an active disease or susceptibility to disease when the disease results from overexpression, underexpression, or altered expression of a Ras-like protein.

Individuals carrying mutations in the Ras-like protein gene can be detected at the nucleic acid level by a variety of techniques. FIG. 3 provides information on SNPs that have been found in the gene encoding the Ras-like protein of the present invention. SNPs were identified at 10 different nucleotide positions. Some of these SNPs that are located outside the ORF and in introns may affect gene transcription. The gene encoding the novel Ras-like protein of the present invention is located on a genome component that has been mapped to human chromosome 17 (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a Ras-like protein gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant Ras-like protein gene and a wild-type gene can be determined by direct DNA sequencing. A variety of automated sequencing procedures can be utilized when performing the diagnostic assays (Naeve, C. W., *Biotechniques* 19:448 (1995)), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include, selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the Ras-like protein gene in an individual in order to select an appropriate compound or dosage regimen for treatment. FIG. 3 provides information on SNPs that have been found in the gene encoding the Ras-like protein of the present invention. SNPs were identified at 10 different nucleotide positions. Some of these SNPs that are located outside the ORF and in introns may affect gene transcription.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control Ras-like protein gene expression in cells, tissues, and organisms. A DNA antisense nucleic acid molecule is designed to be complementary to a region of the gene involved in transcription, preventing transcription and hence production of Ras-like protein. An antisense RNA or DNA nucleic acid molecule would hybridize to the mRNA and thus block translation of mRNA into Ras-like protein.

Alternatively, a class of antisense molecules can be used to inactivate mRNA in order to decrease expression of Ras-like protein nucleic acid. Accordingly, these molecules can treat a disorder characterized by abnormal or undesired Ras-like protein nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the Ras-like protein, such as ligand binding.

The nucleic acid molecules also provide vectors for gene therapy in patients containing cells that are aberrant in Ras-like protein gene expression. Thus, recombinant cells, which include the patient's cells that have been engineered ex vivo and returned to the patient, are introduced into an individual where the cells produce the desired Ras-like protein to treat the individual.

The invention also encompasses kits for detecting the presence of a Ras-like protein nucleic acid in a biological sample. Experimental data as provided in FIG. 1 indicates that Ras-like proteins of the present invention are expressed in humans in prostate, brain, T-cells from T-cell leukemia, and leukopheresis, as indicated by virtual northern blot analysis. In addition, PCR-based tissue screening panels indicate expression in leukocytes. For example, the kit can comprise reagents such as a labeled or labelable nucleic acid or agent capable of detecting Ras-like protein nucleic acid in a biological sample; means for determining the amount of Ras-like protein nucleic acid in the sample; and means for comparing the amount of Ras-like protein nucleic acid in the sample with a standard. The compound or agent can be packaged in a suitable container. The kit can further comprise instructions for using the kit to detect Ras-like protein mRNA or DNA.

Nucleic Acid Arrays

The present invention further provides arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application W095/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et. al., U.S. Pat. No. 5,807,522.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides that are only 7–20 nucleotides in length. The microarray may contain oligonucleotides that cover the known 5', or 3', sequence, sequential oligonucleotides that cover the full-length sequence; or unique oligonucleotides selected from particular areas along the length of the sequence. Polynucleotides used in the microarray may be oligonucleotides that are specific to a gene or genes of interest.

In order to produce oligonucleotides to a known sequence for a microarray, the gene(s) of interest (or an ORF identified from the contigs of the present invention) is typically examined using a computer algorithm that starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application W095/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of one or more of the proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention. FIG. 3 provides information on SNPs that have been found in the gene encoding the Ras-like protein of the present invention. SNPs were identified at 10 different nucleotide positions. Some of these SNPs that are located outside the ORF and in introns may affect gene transcription.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the human genome disclosed herein. Examples of such assays can be found in Chard, T, *An Introduction to Radioimmunoassay and Related Techniques,* Elsevier Science Publishers, Amsterdam, The Netherlands (1986); Bullock, G. R. et al., *Techniques in Immunocytochemistry,* Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology,* Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the human genome disclosed herein; and (b) one or more other containers comprising one or more of the following: wash reagents, reagents capable of detecting presence of a bound nucleic acid. Preferred kits will include chips that are capable of detecting the expression of 10 or more, 100 or more, or 500 or more, 1000 or more, or all of the genes expressed in Human.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified Ras-like protein genes of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in procaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli,* the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual. 2nd. ed.,* Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd. ed.,* Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli, Streptomyces,* and *Salmonella typhimurium.* Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enteroRas-like protein. Typical fusion expression vectors include pGEX (Smith et al., *Gene* 67:31–40 (1988)), pMAL (New England Biolabs, Beverly, MA) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in a host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli.* (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165(1983)) and the pVL series (Lucklow etal., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance, propagation, or expression of the nucleic acid molecules described herein. These are found for example in Sambrook, J., Fritsh, E. F., and Maniatis, T. *Molecular Cloning: A Laboratory Manual. 2nd, ed., Cold Spring Harbor Laboratory,* Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed, Cold Spring Harbor Laboratory,* Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced, or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a Ras-like protein polypeptide that can be further purified to produce desired amounts of Ras-like protein or fragments. Thus, host cells containing expression vectors are useful for peptide production.

Host cells are also useful for conducting cell-based assays involving the Ras-like protein or Ras-like protein fragments. Thus, a recombinant host cell expressing a native Ras-like protein is useful for assaying compounds that stimulate or inhibit Ras-like protein function.

Host cells are also useful for identifying Ras-like protein mutants in which these functions are affected. If the mutants naturally occur and give rise to a pathology, host cells containing the mutations are useful to assay compounds that have a desired effect on the mutant Ras-like protein (for example, stimulating or inhibiting function) which may not be indicated by their effect on the native Ras-like protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a Ras-like protein and identifying and evaluating modulators of Ras-like protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the Ras-like protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the Ras-like protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect ligand binding, Ras-like protein activation, and signal transduction, may not be evident from in vitro cell-free or cell-based assays. Accordingly, it is useful to provide non-human transgenic animals to assay in vivo Ras-like protein function, including ligand interaction, the effect of specific mutant Ras-like proteins on Ras-like protein function and ligand interaction, and the effect of chimeric Ras-like proteins. It is also possible to assess the effect of null mutations, which is mutations that substantially or completely eliminate one or more Ras-like protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention, which are obvious to those skilled in the field of molecular biology or related fields, are intended to be within the scope of the following claims.

That which is claimed is:

1. An isolated nucleic molecule consisting of a nucleotide sequence selected from the group consisting of:

(a) a nucleotide sequence consisting of SEQ ID NO:1;

(b) a nucleotide sequence consisting of SEQ ID NO:3; and (c) a nucleotide sequence that is completely complementary over the entire length of a nucleic acid molecule of (a) or (b).

2. A nucleic acid construct comprising the nucleic acid molecule of claim 1, used to a heterologous nucleotide sequence.

3. The nucleic acid construct of claim 2, wherein the heterologous nucleotide sequence encodes a heterologous polypeptide.

4. A vector comprising the nucleic acid molecule of claim 1.

5. The vector of claim 4, wherein said isolated nucleic acid molecule is inserted into said vector in proper orientation and correct reading frame such that a polypeptide may be expressed by a cell transformed with said vector, wherein the amino acid sequence of said polypeptide consists of SEQ ID NO:2.

6. The vector of claim 5, wherein said isolated nucleic acid molecule is operatively linked to a promoter sequence.

7. An isolated host cell containing the vector of claim 4.

8. A process for producing a polypeptide wherein the amino acid sequence of said polypeptide consists of SEQ ID NO:2, the process comprising culturing the host cell of claim 7 under conditions sufficient for the production of said polypeptide, and recovering said polypeptide, thereby producing said polypeptide.

9. The vector of claim 4, wherein said vector is selected from the group consisting of a plasmid, a virus, and a bacteriophage.

10. An isolated polynucleotide consisting of the nucleotide sequence of SEQ ID NO:1.

11. An isolated polynucleotide consisting of the nucleotide sequence of SEQ ID NO:3.

* * * * *